US009207198B2

(12) United States Patent
Wang et al.

(10) Patent No.: US 9,207,198 B2
(45) Date of Patent: Dec. 8, 2015

(54) ELECTRICAL TOMOGRAPHY APPARATUS AND METHOD AND CURRENT DRIVER

(75) Inventors: Mi Wang, Cheadle (GB); Jiabin Jia, Leeds (GB)

(73) Assignee: The University of Leeds, Leeds, Yorkshire (GB)

(*) Notice: Subject to any disclaimer, the term of this patent is extended or adjusted under 35 U.S.C. 154(b) by 911 days.

(21) Appl. No.: 13/380,010

(22) PCT Filed: Jun. 22, 2010

(86) PCT No.: PCT/GB2010/051035
§ 371 (c)(1),
(2), (4) Date: Dec. 21, 2011

(87) PCT Pub. No.: WO2010/150009
PCT Pub. Date: Dec. 29, 2010

(65) Prior Publication Data
US 2012/0098549 A1    Apr. 26, 2012

(30) Foreign Application Priority Data

Jun. 22, 2009   (GB) .................................. 0910704.6

(51) Int. Cl.
*G01R 27/28* (2006.01)
*G01N 27/02* (2006.01)

(52) U.S. Cl.
CPC .................................... *G01N 27/026* (2013.01)

(58) Field of Classification Search
CPC .................................................... G01N 27/02
USPC ........................................ 324/649, 704, 705
See application file for complete search history.

(56) References Cited

U.S. PATENT DOCUMENTS 3,518,518 A * 6/1970 Ford, Jr. et al. ............... 388/806
3,675,105 A * 7/1972 Petrigalla ...................... 388/826
(Continued)

FOREIGN PATENT DOCUMENTS

EP   1813345 A1   8/2007
GB   2454925 A    5/2009

OTHER PUBLICATIONS

International Preliminary Report on Patentability and Written Opinion of the International Searching Authority, mailed Jan. 12, 2012, for corresponding International Application No. PCT/GB2010/051035, 9 pages.

(Continued)

*Primary Examiner* — Tung X Nguyen
*Assistant Examiner* — Giovanni Astacio-Oquendo
(74) *Attorney, Agent, or Firm* — Klarquist Sparkman, LLP

(57) ABSTRACT

Electrical tomography apparatus comprises: a first electrode; a second electrode; and current driving means for driving an electrical current between the first electrode and the second electrode through a medium, wherein the current driving means comprises: a first transformer having a first winding and a second winding, the second winding having a first terminal and a second terminal; and means for generating an alternating current through the first winding so as to generate an alternating voltage between said first terminal and said second terminal. The apparatus further comprises connecting means arranged to connect the first terminal to the first electrode and the second terminal to the second electrode. Generation of the alternating current in the first winding results in generation of an alternating voltage between the first and second electrodes. In certain embodiments, a current sensing transformer provides an indication of current driven through the medium.

26 Claims, 16 Drawing Sheets

(56) References Cited

U.S. PATENT DOCUMENTS

| | | | | |
|---|---|---|---|---|
| 5,911,160 | A * | 6/1999 | Abe et al. | 73/602 |
| 5,993,391 | A * | 11/1999 | Kamiyama | 600/443 |
| 7,755,299 | B2 * | 7/2010 | Weger | 315/279 |
| 2003/0001595 | A1 | 1/2003 | Steele | |
| 2004/0242989 | A1 * | 12/2004 | Zhu | A61B 5/0536 600/407 |
| 2006/0146338 | A1 * | 7/2006 | Fujita | 356/479 |
| 2007/0010758 | A1 | 1/2007 | Matthiessen | |
| 2008/0058643 | A1 * | 3/2008 | Hashimoto et al. | 600/437 |
| 2009/0251928 | A1 * | 10/2009 | Zheng | H02M 3/3384 363/20 |
| 2010/0060186 | A1 * | 3/2010 | Taipale | H05B 41/2822 315/291 |
| 2010/0303321 | A1 * | 12/2010 | McEwan | A61B 5/0536 382/131 |

OTHER PUBLICATIONS

International Search Report and Written Opinion of the International Searching Authority, mailed Oct. 11, 2010, for corresponding International Application No. PCT/GB2010/051035, 15 pages.

Bolton et al., "Development of an Electrical Tomographic System for Operation in a Remote, Acidic and Radioactive Environment," *Chem Eng Jnl*, vol. 130, No. 2-3, pp. 165-169, May 10, 2007.

Boone et al., "Topical Review; Current Approaches to Analogue Instrumentation Design in Electrical Impedance Tomography," *Physiol Measur*, vol. 17, No. 4, pp. 229-247, Nov. 1, 1996.

Rosell et al., "Analysis and Assessment of Errors in a Parallel Data Acquisition System for Electrical Impedance Tomography," *Clin Phys Physiol Meas*, vol. 9, No. 4A, pp. 93-99, Nov. 1, 1988.

* cited by examiner

• Primary side    ○ Secondary side (a) Bifilar winding    (b) Layer winding ated Application
ELECTRICAL TOMOGRAPHY APPARATUS AND METHOD AND CURRENT DRIVER

CROSS REFERENCE TO RELATED APPLICATIONS

This is the U.S. National Stage of International Application No. PCT/GB2010/051035, filed Jun. 22, 2010, which in turn claims the benefit of Great Britain Application No. GB0910704.6, filed Jun. 22, 2009.

FIELD OF THE INVENTION

One aspect of the present invention relates to electrical tomography apparatus and methods, and certain embodiments relate in particular, although not exclusively, to tomography sensing systems for high conductivity fluids. Certain aspects of the present invention are concerned with apparatus and methods for driving electrical current between a pair of electrodes via a medium, and with electrical test apparatus and methods utilising such current driving apparatus and methods.

BACKGROUND TO THE INVENTION

Certain embodiments of the invention relate to electrical tomography, and may utilise electrode arrangements (e.g. electrode arrays) known in the art. Certain embodiments may also be used for electrical tomography applications known in the art.

Known electrical tomography techniques include electrical impedance tomography (EIT), electrical resistance tomography (ERT), and electrical capacitance tomography (ECT). EIT is known for use as a medical imaging technique in which an image of the conductivity or permittivity are part of the body is inferred from surface electrical measurements. Conducting electrodes are typically attached to the skin of the subject and small alternating currents are applied to some or all of the electrodes. Resulting electrical potentials (i.e. between electrodes) are measured, and the process may be repeated for different configurations of applied current. Investigated processing techniques are used to generate an image of the body or other medium or sample under test, from the current and voltage signals. Applications of electrical impedance tomography are not limited to medical imaging, and indeed embodiments of the present invention may be used in electrical impedance tomography techniques for evaluating any suitable medium or structure (which we may also describe as a sample). ERT also finds a wide variety of applications, and is known for use in geophysics. In this particular application, electrodes may be placed on the surface of the earth or at some other location to locate resistivity anomalies. ERT also finds application in industrial process monitoring, where arrays of electrodes may be used to monitor mixtures of conductive fluids in vessels or pipes. ERT techniques may be used in industrial process imaging for imaging conductive fluids. In this particular context, the technique may be called electrical resistance tomography. In such applications, in which embodiments of the invention may be used, metal electrodes may be placed in direct contact with the fluid (which may be a single fluid or a mixture) to be evaluated.

Electrical capacitance tomography (ECT) is a method for determination of the dielectric permittivity distribution in the interior of an object from external capacitance measurements. ECT is closely related to EIT and may also be used as a method for industrial process monitoring. Potential applications include the measurement of flow of fluids in pipes, and measurement of the concentration of one fluid in another, or the distribution of a solid in a fluid. In ECT, the measurement electrodes may take the form of metallic plates and these should be arranged so as to be sufficiently large to give a measurable change in capacitance. This means that very few electrodes are used and 8 or 12 electrodes are common.

ERT systems typically use a current source to drive an alternating current through a medium to be evaluated. However, problems arise when the medium to be evaluated is a fluid having a relatively high conductivity. Relatively high conductivity means that the equivalent electrical impedance of fluid is low, which means that, for a given current driven by a current source through the medium, corresponding response voltages from electrodes are small. Clearly, output currents from any given current source are limited, and hence measurement of the small voltages developed in or across the medium may be difficult due to the presence of noise. In other words, a low signal to noise ratio is a problem associated with ERT techniques used to evaluate high conductivity fluids. The presence of a common mode voltage is a further problem associated with attempts to use ERT techniques for evaluating high conductivity fluids. A further problem is the handling of large dynamic ranges in voltage signals from measurement electrodes to be digitised (for example by an ADC) so that they can be subsequently processed.

SUMMARY OF THE INVENTION

Certain embodiments of the present invention aim to provide electrical tomography apparatus and methods which solve, at least partly, one or more of the problems associated with the prior art.

According to a first aspect of the invention there is provided electrical tomography apparatus comprising:
  a first electrode;
  a second electrode; and
  current driving means for driving an electrical current between the first electrode and the second electrode through a medium (i.e. a medium to be evaluated, e.g. a medium in contact with the first and second electrodes), wherein the current driving means comprises:
  a first transformer having a first (primary) winding and a second (secondary) winding, the second winding having a first terminal and a second terminal; and
  means for generating an alternating current through the first winding so as to generate an alternating voltage between said first terminal and said second terminal,
  the apparatus further comprising connecting means arranged to connect the first terminal to the first electrode and the second terminal to the second electrode,
  whereby generation of the alternating current in the first winding results in generation of an alternating voltage between the first and second electrodes.

It will be appreciated that, in effect, the current driving means is a voltage source arranged to generate an alternating voltage between the electrodes so as to be able to drive a current through the medium to be evaluated (i.e. a medium directly in contact with the electrodes, or close to the electrodes in the case of the apparatus being used for ECT techniques). This voltage source is in contrast with the current sources typically used in the prior art.

It will be appreciated that the connecting means may be arranged to connect the first terminal to the first electrode either directly or indirectly, and similarly to connect the second terminal to the second electrode either directly or indirectly. For example, in certain embodiments the second terminal is connected to the second electrode via a primary winding of a current-sensing transformer. Thus, the primary winding of that second transformer may form part of the connecting means.

The apparatus in accordance with this first aspect is able to deliver large currents to the electrodes, and consequently large response voltages may be developed on electrodes used for monitoring potentials developed in the medium to be evaluated. Large response voltages on measurement electrodes are beneficial to enhance the signal to noise ratio. Also, the use of the first transformer in the generation of the voltage across the electrodes to drive current through the medium contributes to a high common mode voltage rejection ratio.

In certain embodiments, the apparatus further comprises current sensing means (current sensor) arranged to provide a current signal indicative of current flowing through said second winding, the current sensing means comprising:

a second transformer having a primary winding and a secondary winding arranged such that an alternating current flowing in the primary winding generates a corresponding alternating voltage across the secondary winding, (i.e. between first and second terminals of the secondary winding), the primary winding being connected in series with the second winding of the first transformer such that the same current flows through the second and primary windings, and a voltage developed across the secondary winding providing said current signal.

Thus, this second transformer can be described as a current sensing transformer, providing non-destructive current measurement. The number of turns in the primary winding may be substantially smaller than the number in the secondary winding. For example, in certain embodiments the primary winding may comprise just a single turn, and the secondary winding may comprise 100 turns or more. This means that the primary winding presents a very small impedance to the current being driven through the medium under measurement via the first transformer. By having a large number of turns on the secondary winding, the current signal developed across the secondary winding can be an appreciable voltage, even when the current in the primary winding is low.

In certain embodiments, the apparatus further comprises first amplification means arranged to generate a first amplified signal from said current signal, the first amplification means comprising a first logarithmic amplifier.

Thus, the first amplified signal may be indicative of a logarithm of the current being driven through the medium.

In certain embodiments, the first amplication means comprises a first pre-amplifier arranged to amplify the current signal and provide the amplified current signal as an input signal to the first logarithmic amplifier.

In certain embodiments, the first amplified signal is an output signal of the first logarithmic amplifier.

In certain embodiments, the apparatus further comprises a third electrode and a fourth electrode and second amplification means arranged to generate a second amplified signal from a voltage signal corresponding to or indicative of a voltage (differential voltage) developed between the third and fourth electrodes as a result of (i.e. when) said electrical current being driven between the first and second electrodes through said medium.

It will be appreciated that in certain embodiments the third and fourth electrodes are electrodes in addition to the first and second electrodes. However, in certain embodiments, the first and second electrodes may be used to monitor voltages developed as a consequence of currents being driven in the medium under evaluation, in addition to being used to drive the current.

It will also be appreciated that electrical tomography apparatus embodying the invention may comprise a large number of electrodes, and the first and second electrodes, and the third and fourth electrodes may be electrode pairs selected from that large number. Also, when current is being driven through a particular pair of electrodes, the voltages developed across different pairs of electrodes may be monitored in order to generate data useable to construct an image of the medium under test. Similarly, the apparatus may be used to drive current through different selected pairs of electrodes to generate measurement data.

In certain embodiments, the second amplification means comprises a second logarithmic amplifier, arranged such that the second amplified signal is indicative of a logarithm of the voltage developed between the third and fourth electrodes.

In certain embodiments, the second amplification means comprises a second pre-amplifier arranged to amplify said voltage signal and provide the amplified voltage signal as an input signal to the second logarithmic amplifier.

In certain embodiments, the first amplified signal is an output signal of the first logarithmic amplifier, and the second amplified signal is an output signal of the second logarithmic amplifier.

In certain embodiments, the apparatus further comprises means for generating a difference signal indicative of a difference between the first amplified signal and the second amplified signal. This means for generating a difference signal may, for example, be a differential amplifier. Advantageously, in embodiments where the first and second amplified signals are indicative of logarithms of the driven current and voltage developed between the third and fourth electrodes respectively, the difference signal is then directly indicative of an impedance. Thus, the difference signal can be used as a direct indicator of an impedance of the medium under evaluation or a portion of it, and certain problems associated with the prior art are overcome. These problems included the synchronisation of the results of measurement of the current driven through the sample and the results of voltage measurements of the potential developed between electrodes as a result of the currents being driven.

In certain embodiments, the apparatus further comprises converting means (e.g. an ADC or other suitable means) for converting the difference signal to a digital difference signal. In such embodiments, the apparatus may then comprise processing means arranged to process the digital difference signal, for example to build up a picture of an electrical property or properties of the medium (sample) under evaluation).

In certain embodiments, the connecting means comprises a multiplexer controllable to selectively connect the first and second terminals to a pair of electrodes selected from a plurality of electrodes including the first and second electrodes. Thus, the multiplexer may be used to determine which pair of electrodes from the plurality are used to drive current through the medium. Similarly, the multiplexer may be further controllable to select which pair of electrodes from a plurality of test electrodes are used to measure voltage developed as a result of current being driven through the medium. The multiplexer may therefore be controlled to enable interrogation of different pairs of voltage measurement electrodes, and to excite different pairs of electrodes.

In certain embodiments, the apparatus further comprises means for adjusting (controlling) a phase of the alternating current generated in the first winding.

In such embodiments, the means for adjusting may be arranged to adjust the phase of the alternating current according to a phase of the difference signal. The means for adjusting may therefore comprise means for determining a phase of the difference signal.

In certain embodiments, the apparatus further comprises containment means for containing a fluidic medium to be evaluated, and wherein the first and second electrodes are attached to the containment means so as to be in contact with a fluidic medium contained in the containment means.

This containment means may be a vessel for containing the medium, such as a pipe or section of a pipe in which a fluid medium can be arranged to sit or flow.

It will be appreciated that the wide variety of containment means and associated electrode arrangements known from the prior art may be utilised in embodiments of the present invention.

Similarly, certain embodiments of the invention may comprise any known electrical tomography electrode arrangement or array.

Another aspect of the present invention provides an electrical tomography method for evaluating a medium, the method comprising:

driving an electrical current through the medium and detecting a resultant electrical voltage, characterised in that said driving comprises generating an alternating voltage between a pair of current-driving electrodes by generating an alternating current in a first winding of a first transformer to generate an alternating voltage across terminals of a second winding of the transformer, and connecting said terminals to said pair of electrodes.

Again, use of the first transformer provides the advantage of isolating common mode voltage from the medium under test (i.e. the medium to be evaluated).

In certain embodiments, the method further comprises sensing the current driven through the medium using a second transformer having a primary winding, arranged in series with the second winding of the first transformer, and a secondary winding arranged such that a voltage generated across the secondary winding provides a current signal indicative of the current drive through the medium.

In certain embodiments, the method further comprises using first amplification means to generate a first amplified signal indicative of a logarithm of the electrical current driven through the medium;

using second amplification means to generate a second amplified signal indicative of a logarithm of the resultant electrical voltage; and generating a difference signal indicative of a difference between the first amplified signal and the second amplified signal.

In certain embodiments, the method further comprises determining a phase of said difference signal; and adjusting (controlling) a phase of the alternating current in the first winding according to the phase of the difference signal.

A further aspect of the invention provides apparatus for driving electrical current between a pair of electrodes via a medium, the apparatus comprising:

a first transformer having a first winding and a second winding;

means for generating an alternating current through the first winding so as to generate an alternating voltage across the second winding; and current sensing means comprising a second transformer having a primary winding, connected in series with the second winding of the first transformer, and a secondary winding arranged such that a voltage developed across the secondary winding is indicative of current flow in the second and primary windings.

In certain embodiments, the apparatus further comprises a logarithmic amplifier arranged to amplify the voltage developed across the secondary winding, thereby generating a signal indicative of a logarithm of the current flowing through the second winding and the primary winding.

In certain embodiments, the apparatus further comprises connecting means arranged to connect a pair of electrodes to the second and primary windings.

Another aspect of the present invention provides electrical test apparatus for evaluating at least one electrical property of a medium, the test apparatus comprising:

apparatus in accordance with claim 24 arranged to drive an electrical current between first and second electrodes through the medium and to sense the current driven through the medium; and voltage sensing means arranged to sense a voltage developed across the medium as a result of the current driven through the medium.

In certain embodiments, the electrical test apparatus further comprises first amplification means arranged to generate a first amplified signal indicative of a logarithm of the electrical current driven through the medium;

second amplification means arranged to generate a second amplified signal indicative of a logarithm of the voltage developed across the medium; and means for generating a difference signal indicative of a difference between the first amplified signal and the second amplified signal, whereby the difference signal is indicative (directly) of an impedance.

BRIEF DESCRIPTION OF THE DRAWINGS

Embodiments of the present invention will now be described with reference to the accompanying drawings, of which.

DETAILED DESCRIPTION OF EMBODIMENTS OF THE INVENTION

Figure 1:
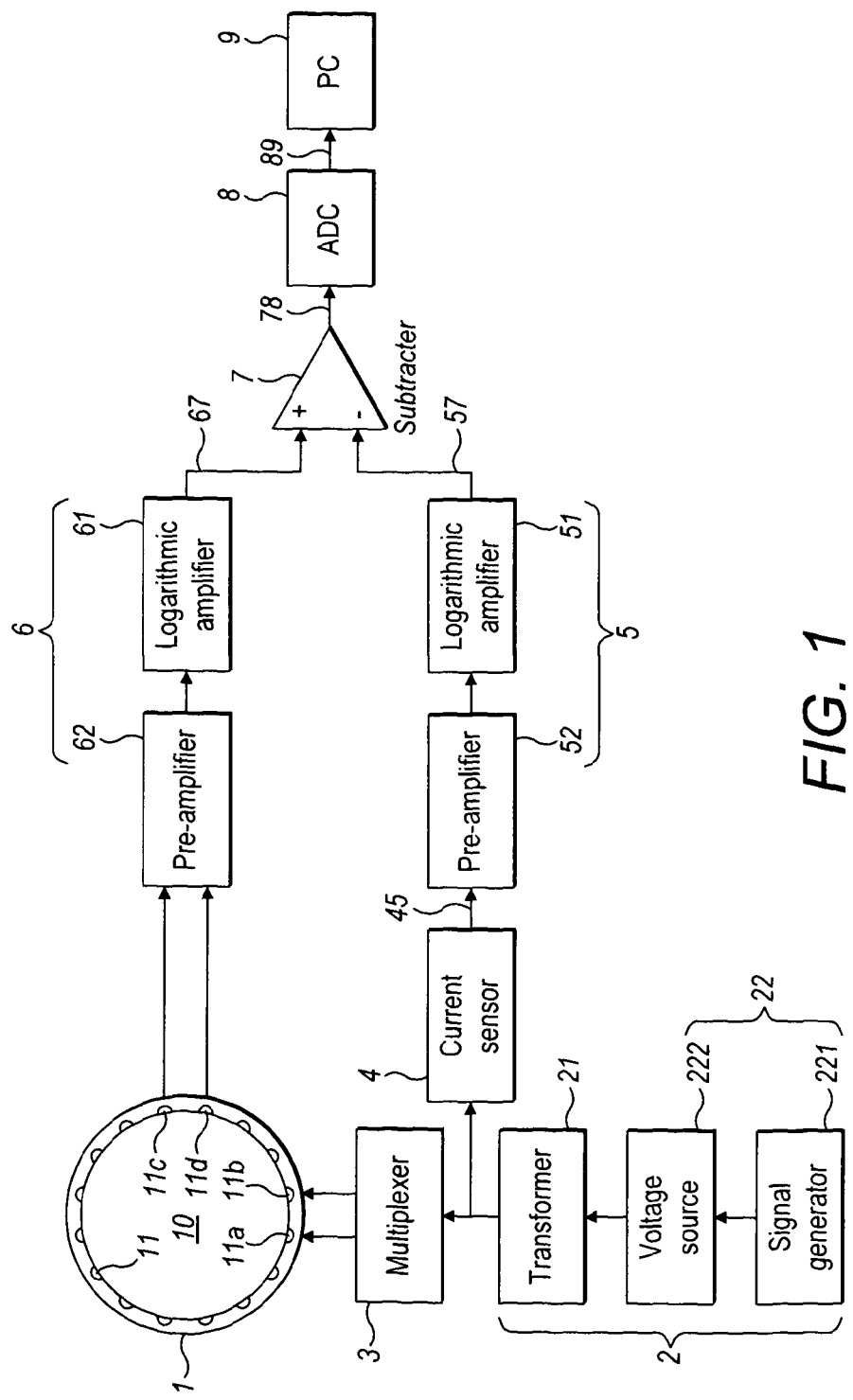
FIG. 1 is a schematic representation of an electrical tomography system embodying the invention.

Referring now to FIG. 1, this shows electrical tomography apparatus embodying the invention. The apparatus comprises containment means 1 having an internal space 10 for containing a medium to be evaluated. A plurality of electrodes 11 are attached to the containment means, and are arranged and spaced apart equally around an inner surface such that each electrode 11 will be in direct contact with a liquid contained in the internal volume 10. These electrodes include a first electrode 11a, a second electrode 11b, a third electrode 11c, and a fourth electrode 11d.

The apparatus comprises current driving means 2 for driving an electrical current between the first electrode 11a and the second electrode 11b through a medium in contact with the electrodes and inside the containment means 1. The current driving means comprises a first transformer 21 having a first winding 211 and a second winding 212, the second winding having a first terminal 2121 and a second terminal 2122. The apparatus also comprises means 22 for generating an alternating current through the first winding of the transformer 21 so as to generate an alternating voltage across the second winding. In this embodiment, the means for generating the alternating current through the first winding comprises a single generator 221 arranged to generate an analog alternating voltage, and a voltage source 222, arranged to receive the alternating voltage signal from the signal generator and amplify it and provide it as a voltage across the first windings 211 of the transformer 21. The apparatus further comprises connecting means in the form of a multiplexer 3 arranged to connect the terminals (i.e. the output) of the transformer 21 to the first and second electrodes 11a, 11b such that the voltage generated in the second winding of the transformer 21 can be used to drive current between the electrodes 11a and 11b. The apparatus also comprises current sensing means 4 arranged to generate a current signal 45 indicative of current flowing through the second winding of the transformer 21 (and hence the current flowing between electrodes 11a and 11b). The apparatus also comprises first amplification means 5 including a preamplifier 52 arranged to amplify the current signal 45 and provide the amplified current signal to a logarithmic amplifier 51. In this example, the output signal of the logarithmic amplifier is a first amplified signal 57 which is indicative of a logarithm of the current flowing between electrodes 11a and 11b. The apparatus also comprises second amplification means 6 arranged to generate a second amplified signal 67 from a differential voltage developed between third and fourth electrodes 11c, 11d as a result of the current driven between electrodes 11a and 11b. This second amplification means comprises a second preamplifier 62 arranged to amplify the voltage signal and provide the amplified voltage signal to a second logarithmic amplifier 61. The second amplified signal 67 is an output signal of the second logarithmic amplifier 61, and is indicative of a logarithm of the voltage developed between the third and fourth electrodes 11c, 11d. The apparatus further comprises a subtractor 7 arranged to provide a difference signal to an analog to digital convertor 8, that difference signal being indicative of a difference between the first amplified signal 57 and the second amplified signal 67. Advantageously, this difference signal 78 is directly indicative of an impedance. The ADC8 converts the analog difference signal 78 to a digital difference signal 89, and provides that digital signal to processing means 9, which may, for example, be a personal computer or other such processing means.

It will be appreciated that the apparatus of FIG. 1 can be used in a method of true impedance measurement in ERT This novel tomographic sensing system can measure the true impedance of the medium to be evaluated (often referred to in the art as the phantom). The system diagram of the voltage-applied electrical resistance tomography (ERT) system is shown in FIG. 1. In principle, the impedance is gained from the differential response voltages ($V_{meas}$), measured on the electrodes and the output current ($I_{meas}$) from the voltage source, as indicated in Eq. (1.1). The voltage $V_{meas}$ and the current $I_{meas}$ are processed synchronously through their own pre-amplifier and logarithmic amplifier. The pre-amplifier controls the input range for the logarithmic amplifier to prevent the saturation. The dynamic range of voltages is a problem for the conventional ERT system. The logarithmic amplifier can automatically adjust the dynamic range of the response voltages and the output current for more accurate measurement. As illustrated in Eq. (1.6), the logarithmic impedance of phantom can be calculated by subtracting the output current ($I_{out}$) from the logarithmic output voltage ($V_{out}$) based on the rule of the logarithmic function. The genuine impedance is obtained by conducting the inverse logarithmic transformation to $V_{out}$-$I_{out}$ (Eq. (1.7)).

$$Z_{meas} = \frac{V_{meas}}{I_{meas}} \quad (1.1)$$

Take logarithm to both sides of Eq. (1.1)

$$\log Z_{meas} = \log \frac{V_{meas}}{I_{meas}} \quad (1.2)$$

Eq. (1.2) can be rewritten as $$Z_{out} = V_{out} - I_{out} \quad (1.3)$$

where, $Z_{out} = \log Z_{meas}, V_{out} = \log V_{meas}, I_{out} = \log I_{meas}$.

In practical realization, some coefficients should be added to adjust their gains and offsets. Then, they can be presented as $$\hat{V}_{out} = \log(k_V V_{meas}) \quad (1.4)$$

$$\hat{I}_{out} = \log(k_I I_{meas}) \quad (1.5)$$

Then, $$\begin{aligned}\hat{Z}_{out} &= \hat{V}_{out} - \hat{I}_{out} \\ &= \log(k_V V_{meas}) - \log(k_I I_{meas}) \\ &= \log\left(\frac{k_V V_{meas}}{k_I I_{meas}}\right) \\ &= \log\left(\frac{k_V}{k_I} Z_{meas}\right)\end{aligned} \quad (1.6)$$

The true impedance can be obtained from $$Z_{meas} = \frac{k_I}{k_V} 10^{(\hat{V}_{out} - \hat{I}_{out})} \quad (1.7)$$

Figure 2:
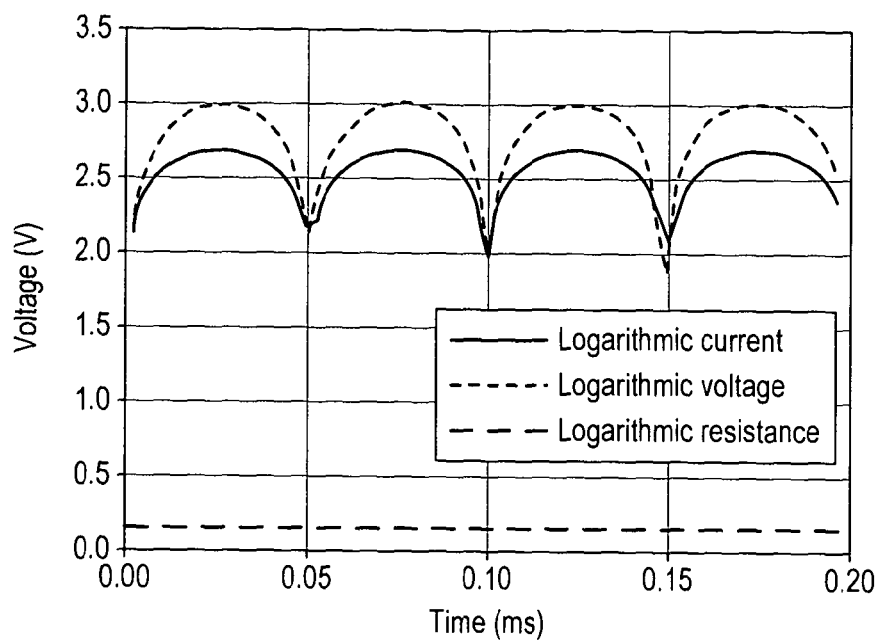
FIG. 2 illustrates the implementation of the logarithmic resistance.

Pure resistor load:

The implementation of the logarithmic resistance to 2 ohm capacitor is shown in FIG. 2. The red dashed lined is the logarithmic resistance derived from the subtraction between the dotted curve (logarithmic voltage) and solid curve (logarithmic current).

Figure 3:
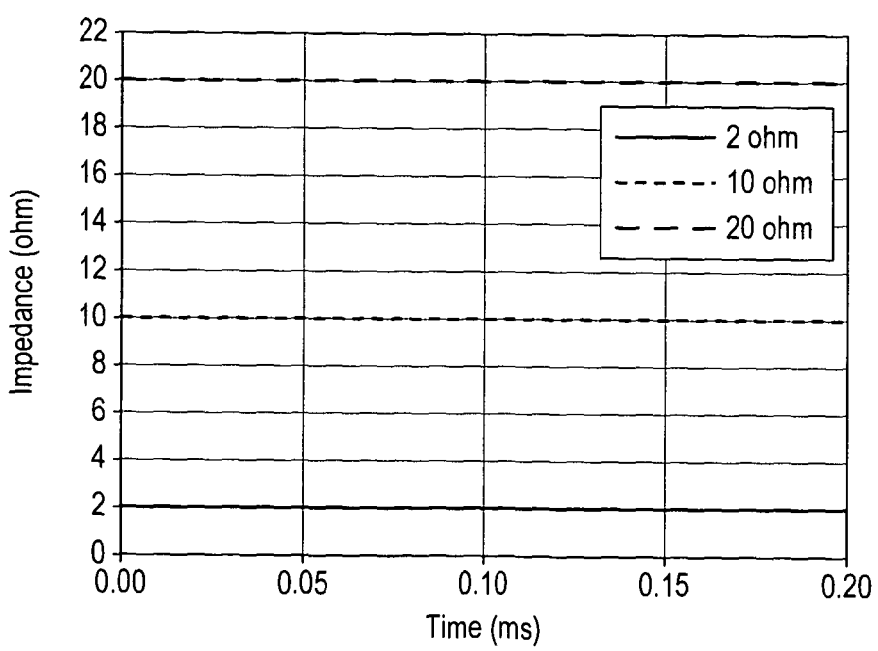
FIG. 3 illustrates the true resistance.
Figure 4:
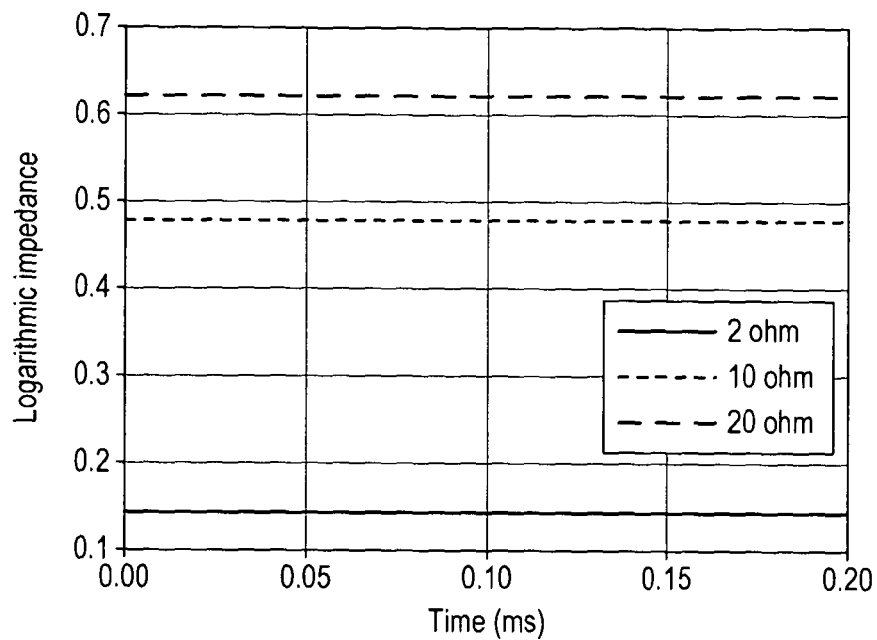
FIG. 4 illustrates the logarithmic resistance.

In FIG. 3, the simulation results calculated from the voltage and current show the true resistance of 2 ohm, 10 ohm and 20 ohm keep constant. According to Eq. (1.6), The logarithmic resistance is simulated and shown in FIG. 4. In terms of the specific logarithmic relationship (Eq. (1.6)), the true resistance of ERT phantom can be inversely derived from the logarithmic resistance.

Pure Capacitor Load

Figure 5:
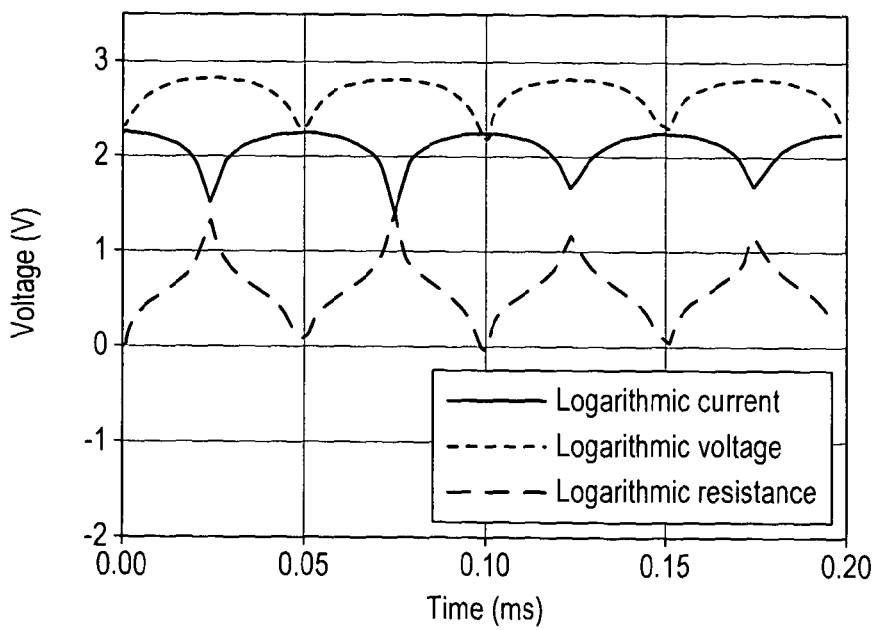
FIG. 5 illustrates the implementation of the logarithmic capacitance.

The implementation of the logarithmic capacitance to 1 uF capacitor is shown in FIG. 5. The red dashed lined is the logarithmic capacitance derived from the subtraction between the dotted curve (logarithmic voltage) and solid curve (logarithmic current).

Figure 6:
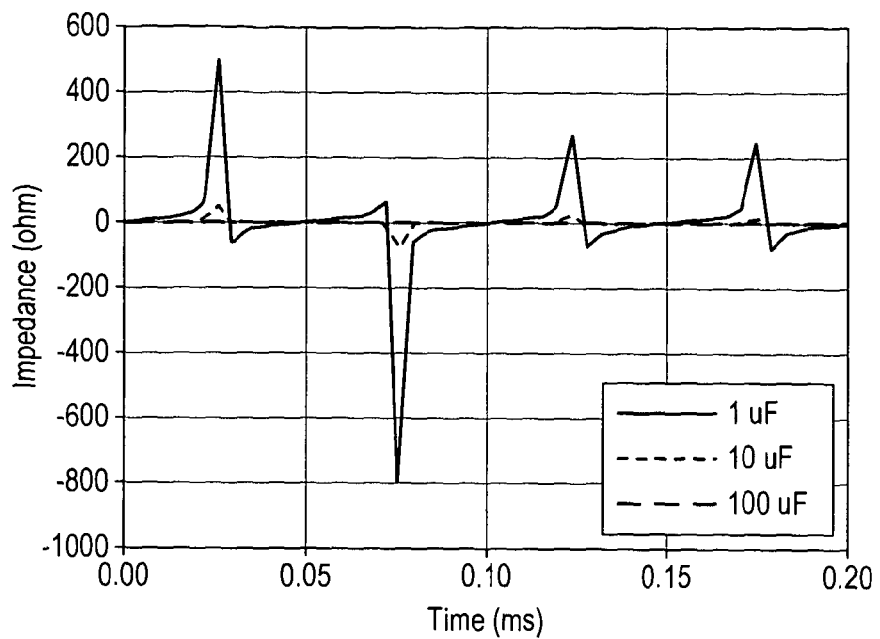
FIG. 6 illustrates the true capacitance.
Figure 7:
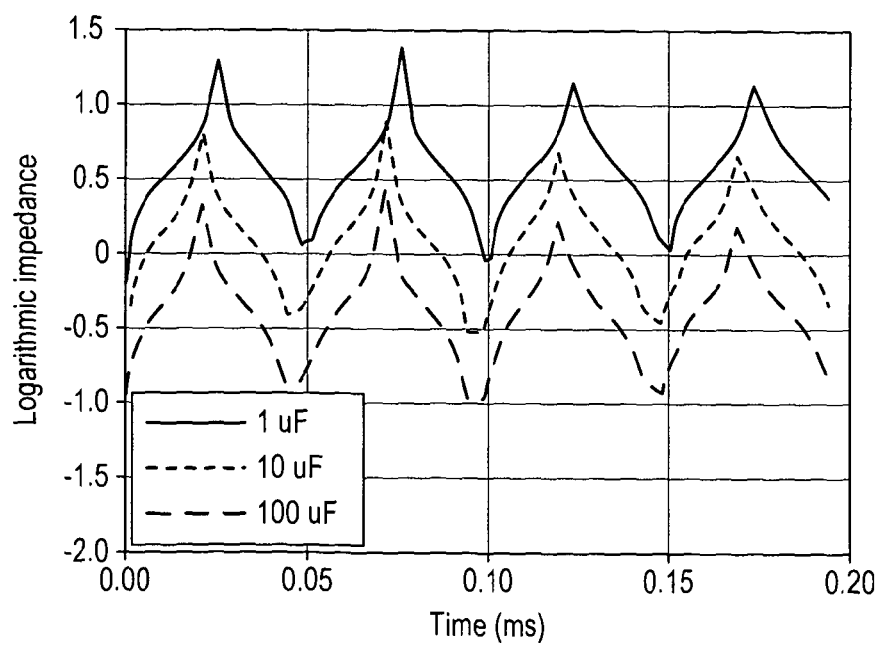
FIG. 7 illustrates the logarithmic capacitance.

In FIG. 6, the simulation results calculated from the voltage and current show the true capacitance of 1 uF, 10 uF and 100 uF keep constant. According to Eq. (1.6), The logarithmic capacitance is simulated and shown in FIG. 7. In terms of the specific logarithmic relationship (Eq. (1.6)), the true capacitance of ERT phantom can be inversely derived from the logarithmic capacitance.

The Phase Optimization Method for an Over-Zero Switching Scheme

Figure 8:
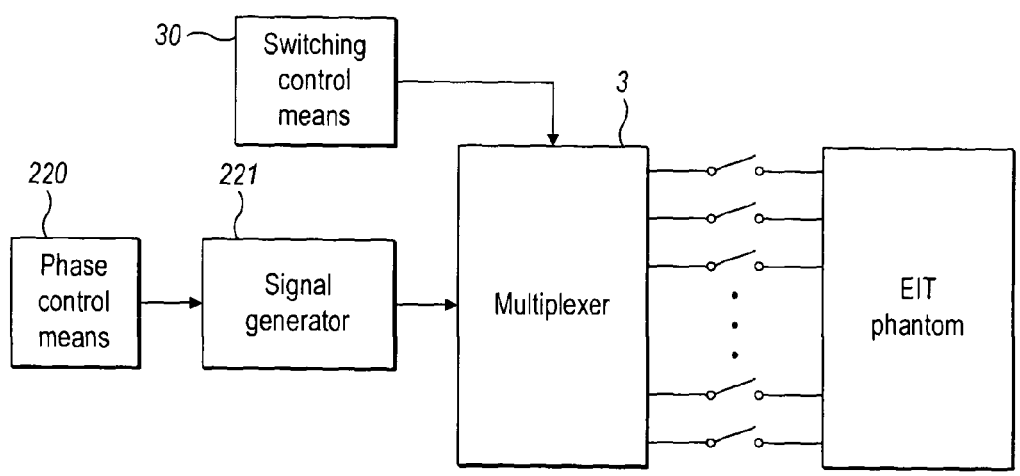
FIG. 8 illustrates the hardware structure of an over-zero switching scheme used in embodiments of the invention.

Certain embodiments employ a phase optimization method for an over-zero switching scheme, as will be appreciated from the following:

As shown in FIG. 8, both controlling the switching timing of the multiplexers and controlling the phase of the signal generator can implement the same over-zero switching scheme. For simplicity, the switching timing of the multiplexers is fixed and the phase control of the signal generator is used for over-zero switching scheme. Phase control means 220 controls the phase of the signal generator, thus controlling the phase of the current driven through the medium. Switching control means controls operation of the multiplexer 3 switches.

In this embodiment:

The hardware circuit includes two layer sensors and 16 electrodes per layer. Potentially, 16 electrodes of one layer can be converted into two layers with 8 electrodes each. The collected data is stored as ASCII format and compatible with the ITS P2000 software. Logarithmic demodulation is employed. An over-zero switching scheme is realized. The maximum current output from the voltage source 222 is 320 mA at 1.8V voltage supply. The maximum speed of system is 300 frames per second. The frequency range is up to 500 kHz, which can be used to measure permeability as a capacitance tomographic system.

Figure 9:
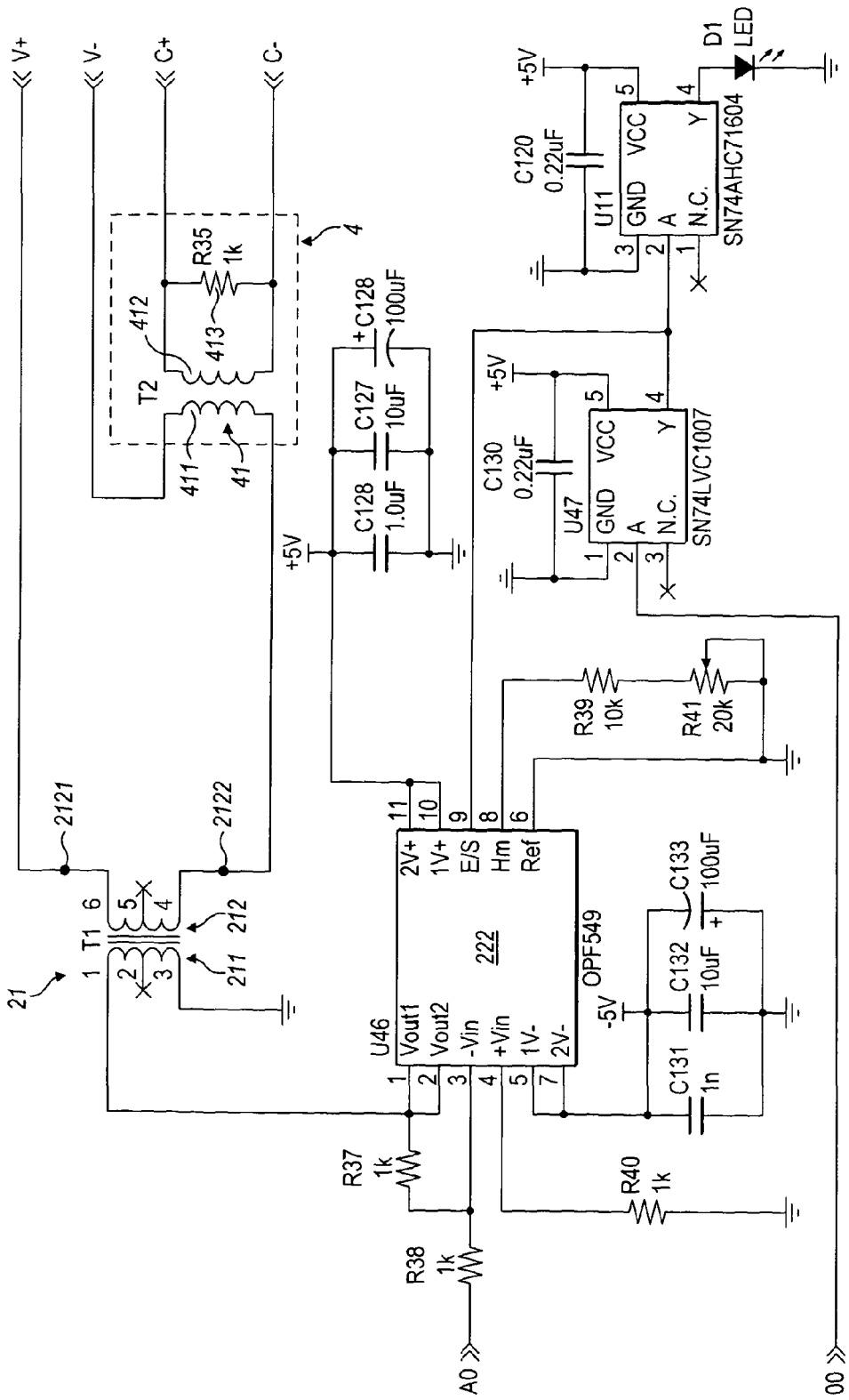
FIG. 9 illustrates the components of current driving means and a current sensor in an embodiment of the invention.

Further information on the above embodiment, and its constituent components, is as follows:

Referring to FIG. 9, this shows the current driving means 2 and current sensor 4 of the first embodiment in more detail. As can be seen, the signal generator 221 provides an analog alternating voltage signal to terminal AO. This analog signal is amplified by power amplifier U46, which thus forms the voltage source 222. This amplified voltage is then applied across the first winding 211 of the first transformer (i.e. between a terminal of the first winding 21 and ground). Although first and second terminals 2121 and 2122 of the second winding 212 are labelled in the figure, it will be appreciated that these are shown at arbitrary positions. The use of the term "terminals" in connection with the windings is simply intended to facilitate description of voltages developed across the windings, and does not necessarily imply that any terminal structure can be identified at any particular location. As can be seen from the figure, the primary winding 411 of the second transformer 41 is connected in series between the second terminal 2122 and a terminal labelled as V−, which is for connection to a second electrode. The first terminal 2121 is directly connected to a terminal V+, for connection to the first electrode. The current sensing means 4 comprises the second transformer 41, and a signal (a voltage) is developed across terminals C+ and C− as a result of alternating current flowing in the primary winding 411. That voltage (which will be described as a current signal, as it is indicative of current flowing in the primary winding 411) is provided to the first amplification means.

It will be appreciated that the embodiment illustrated in FIGS. 1 and 9 represents novel voltage-applied ERT apparatus. The apparatus utilises a voltage source, rather than a current source, for driving current through the phantom.

A large current excitation is essential to enhance the measurement sensitivity of electrical resistance tomography (ERT). The ERT with voltage source can overcome the measurement challenge in high conductive flows.

In FIG. 9, the analog signal from the signal generator is amplified by a power amplifier (U46) first. Then the output goes through a layer winding transformer (T1) 21 to isolate the common mode voltage. The V+ and V− are the final output of voltage source exciting the electrodes.

Current sensing transformer (T2) 41 is connected with the secondary 212 of transformer T1 in series and provides non-destructive current measurement. The main specifications of T2 are listed below.

Turns (N) primary: secondary: 1:200
Inductance on the secondary side: 80 mH
Frequency range (kHz): 1-500
Sensed current range: 5 mA-35 A So, the equivalent resistance of primary side at 10 kHz is only 0.126Ω which causes the miniature voltage drop on it. The voltage on the R35 is related with the primary current. The data acquisition device samples the voltage signal from C+ and C−.

Figure 10:
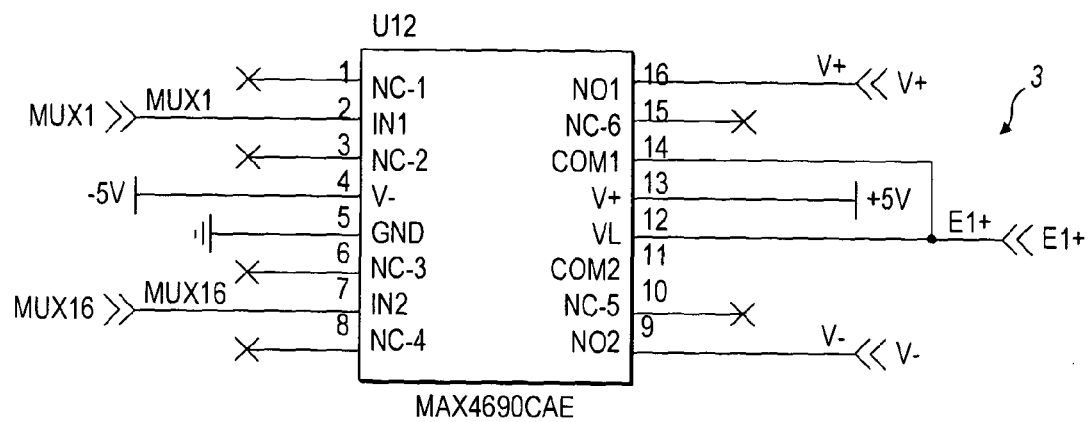
FIG. 10 illustrates a high operational current multiplexer used in embodiments of the invention.

As described above, a multiplexer 3 is used to channel the excitation source to the electrodes and always is the bottleneck of handling large current. The chosen multiplexer (U12) for certain embodiments is shown in FIG. 10, and allows ±200 mA continuous current and ±300 mA peak current (pulsed at 1 ms 10% duty cycle max) to go through the electrodes. Its operation bandwidth is 12.5 MHz and the on-resistance is 1.25 Ω. In FIG. 10, the MUX1 and MUX16 are switch control signals, the V+ and V− are from the secondary side of transformer and the E1+ goes to one of electrodes.

Details of a Logarithmic amplifier (usable as 51 and/or 61 in FIG. 1) are as follows, with reference to FIG. 11.

A programmable gain amplifier only regulates the amplitude of analog signal using the discrete gains, which lowers process speed and induces more errors. The logarithmic amplifier used by embodiments of the invention performs a more complex continuous operation than classical linear amplifiers. Although amplification is embedded inside, the essential purpose of a Log Amp is not only to amplify but also to compress signal with wide dynamic range and yield the logarithm of the rectified signal's envelope.

Figure 11:
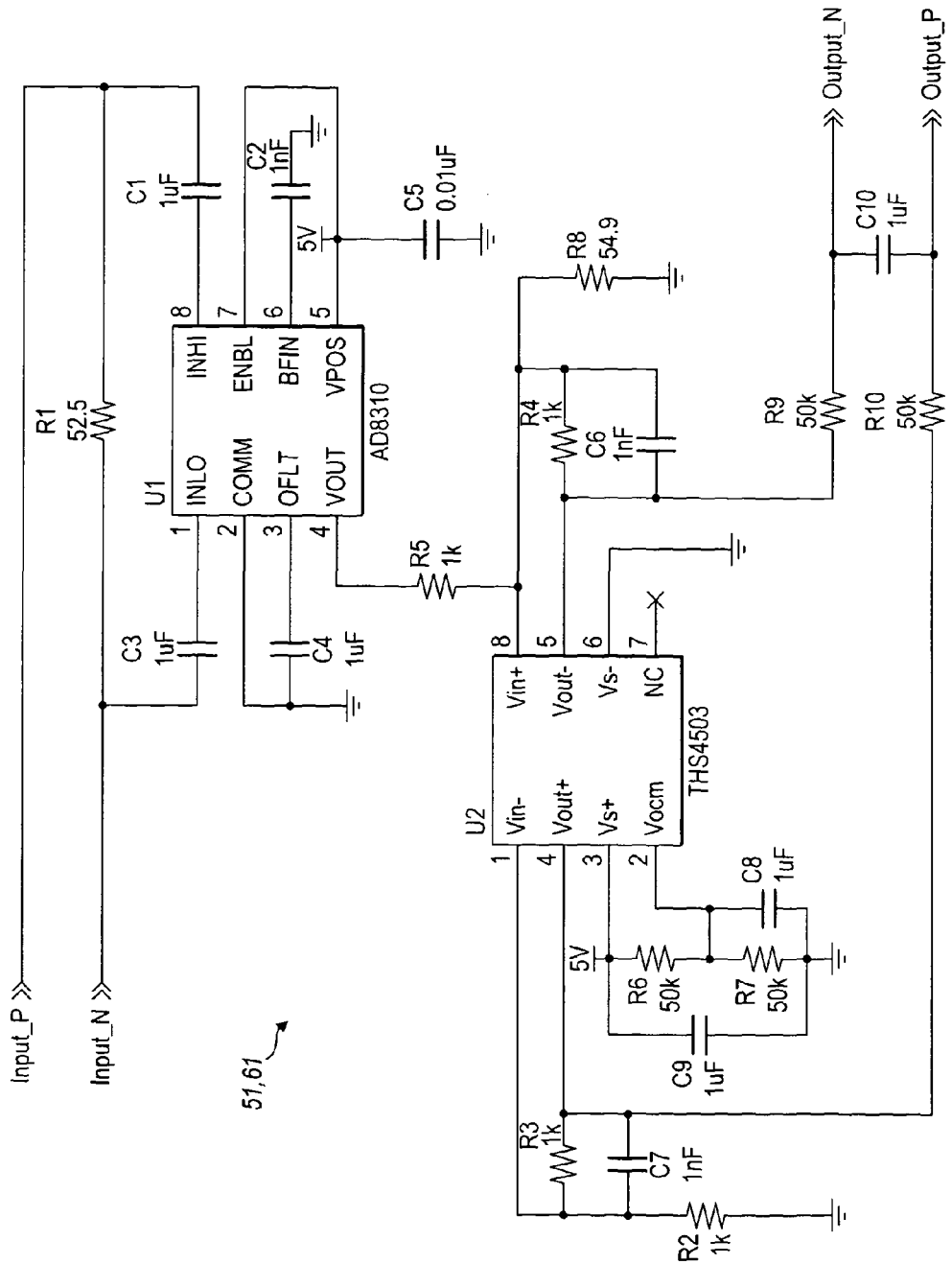
FIG. 11 illustrates a logarithmic amplifier used in embodiments of the invention.

In FIG. 11, a pair of differential signal (Input_P and Input_N), which may be the current signal from the current sensor, or the voltage signal from third and fourth electrodes, or a signal derived therefrom, is converted by the logarithmic amplifier U1. The demodulated single-end signal by U1 becomes the differential signal (Output_P and Output_N) through U2 for the analog-to-digital conversion. The capacitor C2 connected to pin6 of U1 reduces the bandwidth of the output stage and increases the accuracy of the output log voltage, which makes U1 perform extremely well at low frequencies.

In certain embodiments, at the low frequency range (10 kHz~1 MHz) the output of Logarithmic amplifier may have periodic ripples rather than the ideal DC signal. To remove the ripples the following methods may be used: Passive filter; Digital filter; Phase sensitive demodulation; and Numerical integration.

As will be appreciated, Transformer T1 isolates the primary side (voltage source) and secondary side (load). No reference point to ground exists, therefore common mode voltage cannot be formed ideally. Capacitors C126-C133 in FIG. 9. filter the AC noise in the ±5V DC power supply. The components U11 and U47 alarm and protect the power amplifier from the overload. The voltage corresponding to the sensing current is formed on the resistor R35. The parameters of capacitor $C_1$, $C_2$ and $C_3$ are optimized in a Pspice simulation.

Certain embodiments provide a tomography Sensing System for High conductive fluids.

High Sensitive measurement could not be achieved without large current excitation in Electrical Resistance Tomography (ERT). In practice, it will be very difficult to create a current source with large amplitude and high output impedance at a high excitation frequency. Applying the voltage source and current sensing technique to ERT, in embodiments of the invention, can produce larger current than the conventional current source. The specific multiplexers deliver large current to electrodes. Consequently, large response voltages appearing on the electrodes are beneficial to enhance the signal-to-noise ratio. The use of the transformer coupling can contribute a higher common mode voltage reject ratio. Finally, the scheme of using logarithmic amplifier in the signal conditioner of ERT system has significant advantages for the process of signal with a wide dynamic range and for the reduction of gain error, as well as the signal settling time than the conventional programmable gain amplifier. The demodulation of logarithmic waveform still can be implemented by using a new method. The optimal switching timing can be obtained on-line to eliminate the transient time and increase the system speed.

Prior art is disclosed in Reference: Bolton, G. T., M. Bennett, et al. (2007). "Development of an electrical tomographic system for operation in a remote, acidic and radioactive environment", Chemical Engineering Journal 130(2-3): 165-169. Bolton, G. T. conducted a research to handle high conductive solution for acidic and radioactive environment. The pre-amplifier was used to enlarge the signal and average a large number of measurement values to enhance signal-to-noise ratio, however, the speed of measurement was considerably affected.

Advantageous features of embodiments of the invention include the following:
(1) Voltage source for large current excitation (an easy realization of large current output up to 300 mA)
(2) Transformer for isolation common mode voltage (excellent Common voltage rejection ratio)
(3) Multiplexer with high operational current
(4) Current sensing transformer for non-destructive current measurement (it is necessary to measure current. It has an obvious advantage over the conventional current sensing method with a small resistor)
(5) The use of logarithmic amplifier to replace conventional programmable gain amplifier in order to enhance the capability of measurement dynamic range and accuracy
(6) The traditional phase sensitive demodulation method can not be used for the logarithmic waveform. The harmonic can be demodulated, then the original sinusoidal input is demodulated indirectly.
(7) Investigated the relationship between the impedance phase and over zero switching timing. Implemented a new online method to calculate the impedance phase, therefore, the selection of the over zero switching timing can be automatically determined and the transient time is eliminated and the quality of measurement is greatly enhanced
(8) Compact, low-cost and optimised whole ERT system
(9) The data collection speed is about 300 frames/sec for 16 electrode sensor
(10) The method of true impedance measurement Embodiments of the invention may be utilised in the following, non-exhaustive list of applications: Emergent requirement from industries involving high conductive flows in their process, etc offshore oil field, dredging and nuclear industry.

Details of further embodiments are as follows:

One embodiment provides a Novel Tomographic Sensing System for High Conductivity Multiphase Flow Measurement.

The equivalent electrical impedance of water-based multiphase flow in a pipeline decreases with the increasing of continuous phase conductivity. As a result, responding voltages from electrodes shrink greatly which makes the measurement with electrical resistance tomography (ERT) system more difficult. This description introduces an implementation of a novel sensing electronics to overcome the challenge from high conductive multiphase flow measurement. The new sensing system applies a voltage source with a precise current measurement to replace the conventional current source, allowing a maximum current excitation up to 400 mA. It also reinforces a high common voltage rejection ratio at a high excitation frequency range. A logarithmic demodulator is employed to handle the wide dynamic measurement range without the use of programmable gain amplifier and to simplify the structure of signal condition. Therefore, a good signal to noise ratio over a wide dynamic range is achieved. Experimental results from preliminary tests are also reported.

To extract the correct information about two-phase flows with electrical resistance tomography (ERT) comprises a few of essential procedures, for example, generating the excitation source, conditioning the response signal and acquiring and processing the data. If any one of steps introduces noises, the final measurement could present significant errors. There are three key factors affecting on whole process, which are the signal-to-noise ratio (SNR), common mode voltage (CMV) and dynamic measurement range (DMR). Because the conventional ERT with a current source has a limited current output capability (typically, less than 75 mA) and a finite output impedance, the response voltages on the electrodes would be very weak comparing the level of noises if the continuous phase is high conductive. The low SNR at the condition is definitely harmful to the precision of measurement.

CMV is always inherent in conductivity measurements from electrolyte due to the effect of the electro-electrolyte interface. Provided that the adjacent strategy is applied, e.g. with a current of 15 mA, the smallest differential boundary voltage is in the order of millivolt appeared on the pair of electrodes opposite to the source electrodes. Comparing the millivolt, the CMV could be several volts. Although an operational amplifier (Op-Amp) is able to amplify small signals emerging in a high common mode noise and it has a reasonable common mode voltage rejection ratio (CMRR), the CMRR of Op-Amp is normally finite due to the presence of the difference between the mismatched input impedances of the two inputs. Therefore, it is important to design an optimized sensing electronics to reduce the inherent common voltage of ERT sensors. A common mode voltage feedback (CMFB) can provide 40 dB improvement of effective CMRR. The reason of using CMFB technique is due to no common ground allowed for human examination equipment. Therefore, a "virtual" reference with a zero potential has to be created.

However, common mode feedback schemes may cause stability problems, especially in multi-frequency systems. In process engineering application, the CMFB technique is normally not applied. A grounded floating measurement (GFM) scheme is simple and widely used, in which an unused electrode is connected to ground providing a voltage reference to the sensor excited by floating current source(s). The metal wall phantom scheme is other method to reduce the error caused by CMV.

Without any preprocessing, it is difficult for analogy-to-digital converter (ADC) to deal with large dynamic ranges. In order to fully utilize the resolution of ADC, the input signals should be amplified to meet the scale of the ADC. As for the signals with a large dynamic range, the use of programmable gain amplifier (PGA) is always a typical method. However, it is at the cost of complexity on switching circuit and the long signal settling time from a multi-channel ERT system.

In the multiphase flows, if the continuous phase is high conductivity, a larger current value for excitation is required in order to enhance the measurement sensitivity. In practice, it will be very difficult to create a current source with a large amplitude and high output impedance at a high excitation frequency. A voltage-applied ERT system is developed to overcome the measurement challenge from highly conductive multiphase flows.

Figure 12:
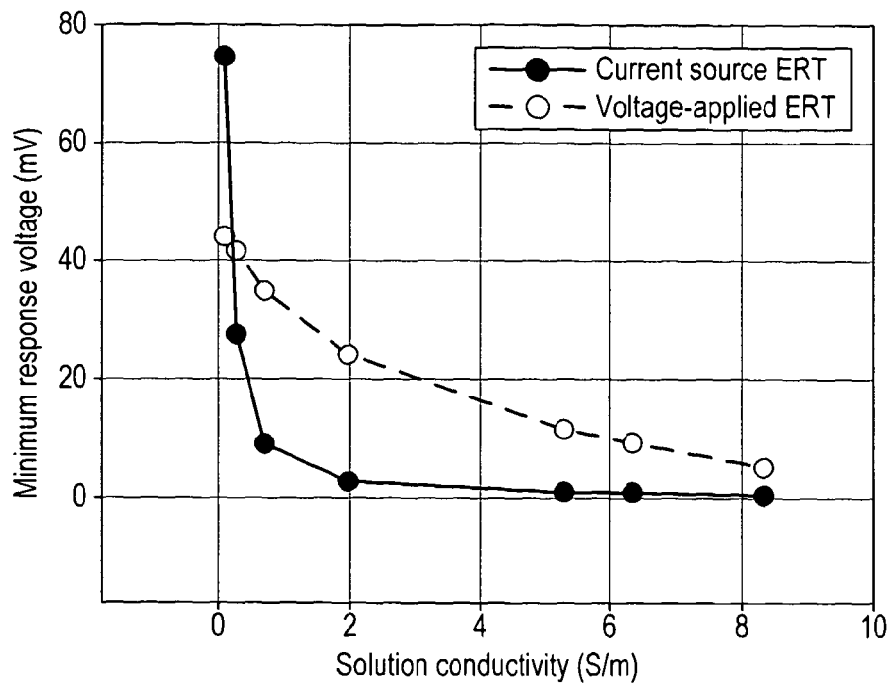
FIG. 12 to FIG. 28 illustrate further features and characteristics of embodiments of the invention and components thereof.

Two basic approaches may improve the SNR. One is to decrease the amplitude of the unwanted noise, which will be discussed later. Another is to increase the amplitude of the wanted signal. It is also necessary to maintain the amplitude of the voltage source unchanged over a wide range of the load impedance and measurement periods. Therefore the voltage source must have a low output impedance. As for ERT system with a current source, the response voltage shrinks dramatically when the conductivity of the solution rises, for example, the differential voltage on a pair of adjacent electrodes opposite to the excitation electrodes reduces from 74.2 mV to 0.2 mV with an increment of continuous phase conductivity from 0.081 S/m to 14.860 S/m (the solid curve in FIG. 12). Meanwhile, for a voltage-applied ERT, the differential voltage changes from 43.5 mV to 4.7 mV (the dotted curve in FIG. 12). Normally, it is difficult for ADC to accurately capture very small voltage values since an ADC chip can make the use of more digital bits for a large voltage input than that for a small one.

Figure 13:
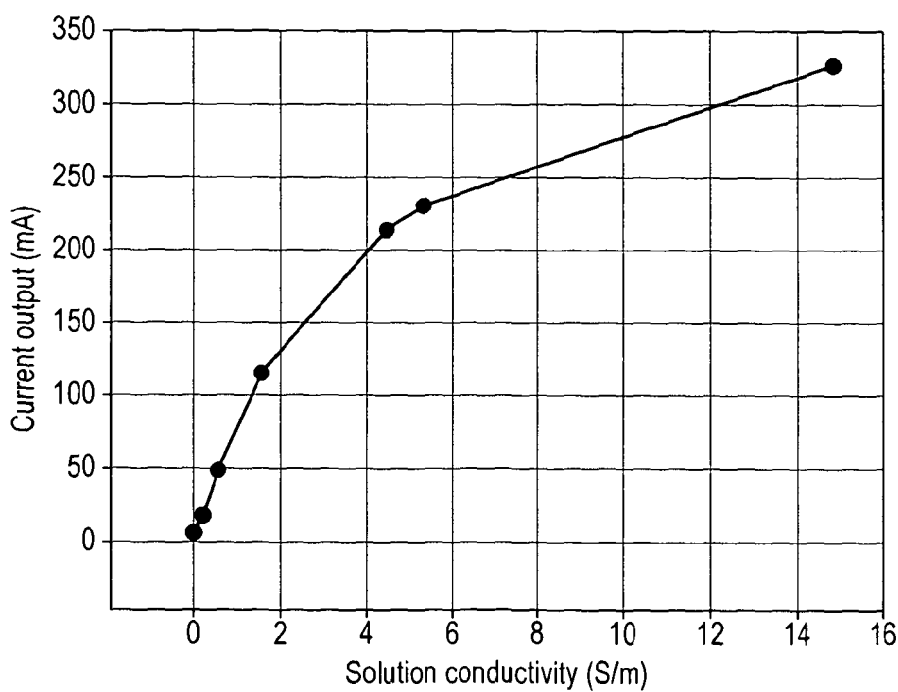

FIG. 13 shows the relation between the output of current and conductivity of solution. The ERT system with a voltage source is able to supply more current to the vessel in which the conductivity of solution increases.

Figure 14:
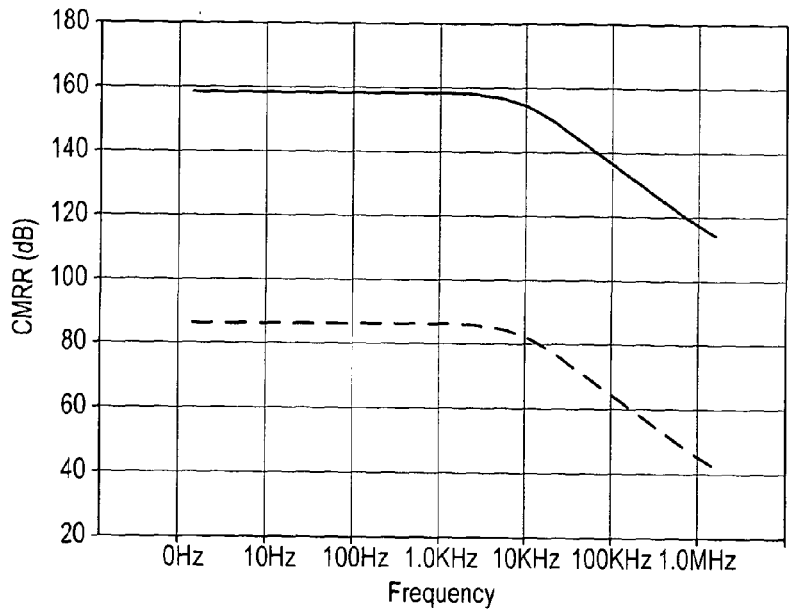

An ideal transformer is capable of transferring the signal from the input winding to the output winding via electromagnetic coupling with a minimum amount of distortion in amplitude and with immunity to the common mode signal. AC voltage is coupled to a balanced transformer that behaviors as a voltage isolation barrier. Voltage isolation means that the portion of the measurement channel corresponding to the input, multiplexer and all front signal process devices is 'floating' with respect to the voltage output and the secondary coil is not referenced or coupled to the measurement instrument ground. With assistance of the Pspice simulator, the CMRR of an amplifier with the transformer coupling is simulated as shown in FIG. 14 (the solid curve), which demonstrates the improved performance, comparing with that obtained from a direct coupling to a commercial differential amplifier (the dotted curve at Gain=1, CMRR=86 dB at 0 Hz, 80 dB at 10 kHz and 40 dB at 1 MHz).

Figure 15:
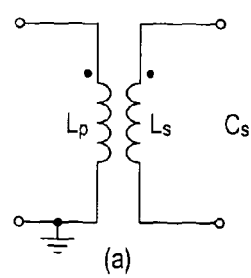
Figure 15:
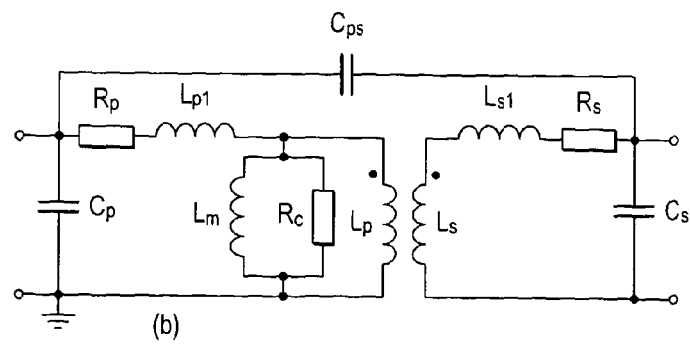

FIG. 15 shows the ideal and real transformer circuits. In FIG. 15($a$), $L_p$ is the primary inductance and $L_s$ is the secondary inductance. In fact, besides $L_p$ and $L_s$, a transformer contains other equivalent elements (FIG. 15($b$)). $L_{p1}$ and $L_{s1}$ are the primary leakage inductance and the secondary leakage inductance respectively; $R_p$ and $R_s$ are DC resistance of the primary and secondary coils; $L_m$ and $R_c$ are shunt inductance and resistance in parallel with the primary coil; $C_p$ and $C_s$ are primary and secondary shunt and distributed capacitance; is primary-to-secondary capacitance that makes an absolute isolation quite difficult. As shown in equation (1), since the impedance of $C_{ps}$ ($X_{Cps}$) will decrease as the frequency of AC signals (f) increases considerably, the isolation function of transformer will attenuate.

Figure 16:
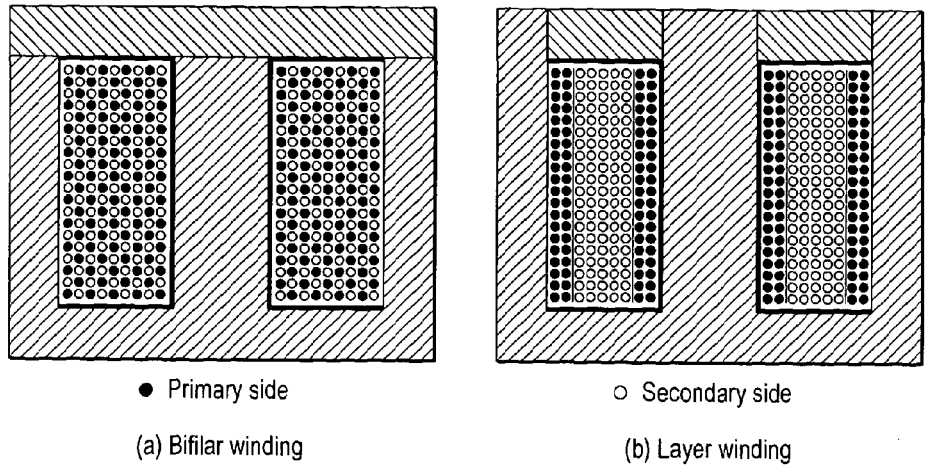

The degree of flux coupling between primary and secondary coils depends on the physical spacing between them and how they are wound with respect to each other. If two windings are wound as one, the transformer is called Bifilar winding (FIG. 16($a$)). The wires of primary and secondary coils are side-by-side throughout; the capacitances $C_{ps}$ can be quite high. The undesirable capacitances $C_{ps}$ could be inhibited by using a layer winding (FIG. 16($b$)) and even completely eliminated with Faraday shield to intercept the capacitive current which would otherwise flow between transformer windings. In the current embodiment, the layer winding transformer is applied.

The signal conditioning circuits mainly consist of a voltage buffer, a high pass filter and amplifiers which are isolated from the ERT sensor with the coupling transform. It functions to remove unwanted signals, limit the signal's spectrum and modify the dynamic range, therefore to maximize the accuracy and sensitivity of data acquisition system (DAS). A rule of thumb for an accurate ADC is to scale the input signal to match the maximum input range of the ADC.

Figure 17:
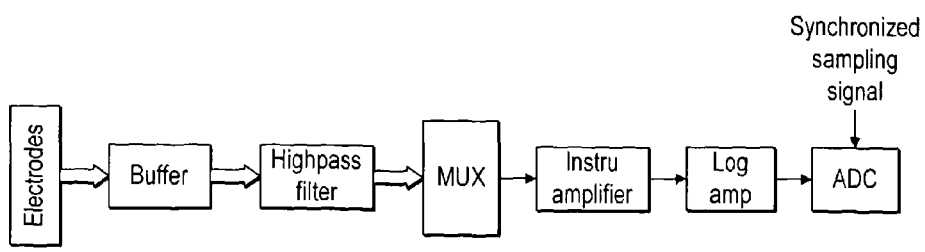

In the proposed circuit, provided that a voltage (3V) is applied to a pair of adjacent electrodes and differential voltages are measured from other pairs of adjacent electrodes, these differential voltages may be as small as 0.0362 V and as large as 2.9504 V in the same voltage profile of a projection with a dynamic range of about 38.2 dB. The typical voltage profile (the solid curve) is shown in FIG. 17, where more than half of data is less than 0.13V. For a 12-bit, 5V input ADC, only low 7 bits can be used for the analog to digital conversion. Additionally, the overwhelming difference may make a quite difficulty for the ADC having an accurate conversion value. Since the image reconstruction algorithmic of ERT is sensitive to errors, any slight original error may result in an enormous error in the reconstructed image. Therefore, any source that might cause an error can not be ignored in the signal conditioner. Normally, a programmable gain amplifiers (PGA) were applied to adjust the amplitudes of signals. The equation (2) denotes a classic relation between the input and output of PGA.

$$V_{OUT} = \begin{cases} 1000 \times X_{IN}, & (0 < |V_{IN}| \le 0.01) \\ 100 \times X_{IN}, & (0.01 < |V_{IN}| \le 0.1) \\ 10 \times X_{IN}, & (0.1 < |V_{IN}| \le 1) \\ 1 \times X_{In}, & (1 < |V_{IN}| \le 10) \end{cases} \quad (2)$$

However, the use of PGA commonly only regulates the amplitude of analog signal in discrete gains (the derivative of equation (2) is shown in the equation (3)), which may cause mismatch between different voltage amplitudes and between different channels due to gain error and individual difference of PGAs.

$$\frac{dV_{OUT}}{dV_{IN}} = \begin{cases} 1000, & (0 < |V_{IN}| \leq 0.01) \\ 100, & (0.01 < |V_{IN}| \leq 0.1) \\ 10, & (0.1 < |V_{IN}| \leq 1) \\ 1, & (1 < |V_{IN}| \leq 10) \end{cases} \qquad (3)$$

Usually, a larger closed-loop gain leads to a larger gain error. For example, the gain err of a commercial programmable gain amplifier (PGA202) is 6% when its gain is 1000 and its working frequency is 100 kHz. In addition, the larger gain also results in a longer signal response time. The typical settling time is 10 μs at 1000 gain for the PAG202, which is one fifth of the period of the signal frequency 20 kHz. Whereas, the settling time of the logarithmic amplifier introduced is 40 ns. Therefore, the offset adjustment and full-range calibration is normally required for a PGA after the change of its gain in order to eliminate the side effect of PGA, which rather slows the speed of ERT system and complicates the operations.

It is therefore to utilize the demodulating Log Amp to compress and demodulate AC input signals, yielding the logarithm of the rectified signal's envelope. The new structure of the signal conditioner is illustrated in FIG. 17. The signals sensed from each electrode are followed by an AC coupling buffer and then, a high-pass filter. A multiplexer decides which pair of differential signals is to be selected for the instrumentation amplifier whose output is converted by a Log Amp before the analog to digital conversion. A sampling signal synchronized with the voltage source controls the timing of the analog to digital conversion. The combination of a Log Amp and a conventional ADC can reduce the problems caused by the PGA as discussed in a previous paragraph as well as simplify the circuitry.

Logarithmic amplifiers perform a more complex operation than classical linear amplifiers, and their circuits are significantly different. Although amplification is embedded inside, the essential purpose of a Log Amp is not to amplify but to compress a signal of wide dynamic range to its decibel equivalent. Its basic function is the conversation of a signal from one domain of representation to another, via a precise non-linear transformation (equation (4)).

$$V_{OUT} = V_Y \log\left(\frac{V_{IN}}{V_X}\right) \qquad (4)$$

Where: $V_{OUT}$ is the demodulated and filtered output voltage; $V_Y$ is the slope voltage (the typical value is 0.5V). The logarithm is usually taken to base ten, in which case $V_Y$ is also the volts-per-decade; $V_{IN}$ and $V_X$ are the input voltage and the intercept voltage. Transfer the equation (4) in RF system's way (Texas instruments) as equation (5) below.

$$V_{OUT} = V_{SLOPE}(P_{IN} - P_O) \qquad (5)$$

Where: $V_{OUT}$ is the demodulated and filtered baseband output (V); $V_{SLOPE}$ is the logarithmic slope; $P_{IN}$ is the input power (dBV), defined as decibels with respect to a 1 V rms sine wave ($V_o$); $P_O$ is the logarithmic intercept (dBV). The equation (6) illustrates the calculation between dBV and V.

$$dBV = 20\log\left(\frac{V_{IN}}{V_0}\right) \qquad (6)$$

Figure 18:
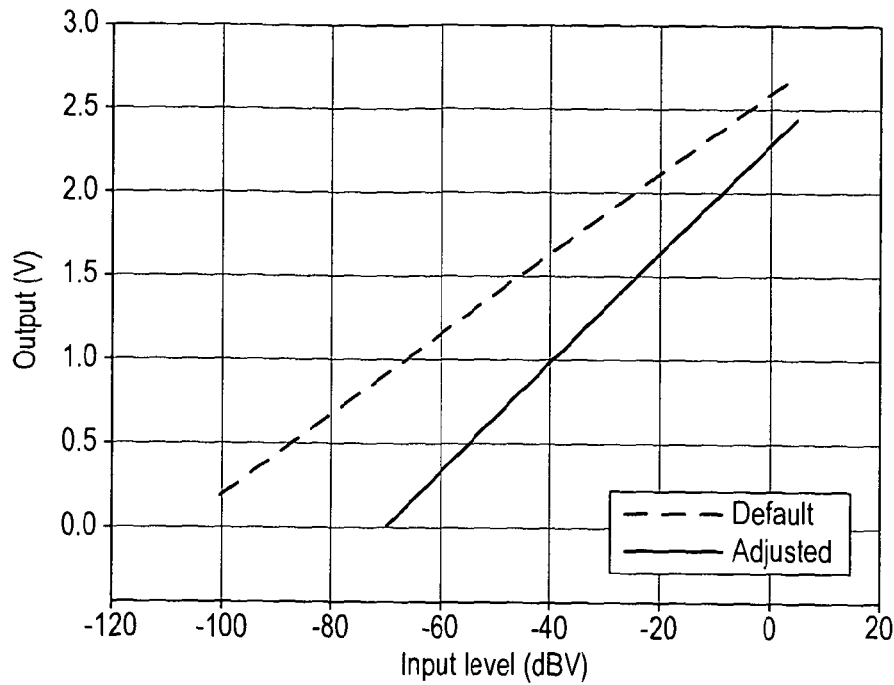

Now, the output voltage is proportional to the Log of the input power, with an adjustable slope and intercept by external resistors configuration to suit the different input range. In FIG. 18, the default relation between the input and output of Log Amp is shown in the dotted line; the solid line indicates the adjusted relation. So, the minimum working input range could be changed from 0.01 mV 0.3 mV.

The Log Amp function described by equation (4) differs from the equation (2) of a linear PGA. Comparing with the incremental gain described in equation (3), equation (7) is a very strong non-linear function of the instantaneous value of $V_{IN}$ by calculating the derivative of equation (4).

$$\frac{dV_{OUT}}{dV_{IN}} = \frac{V_Y}{V_{IN} \cdot \ln(10)} \qquad (7)$$

Figure 19:
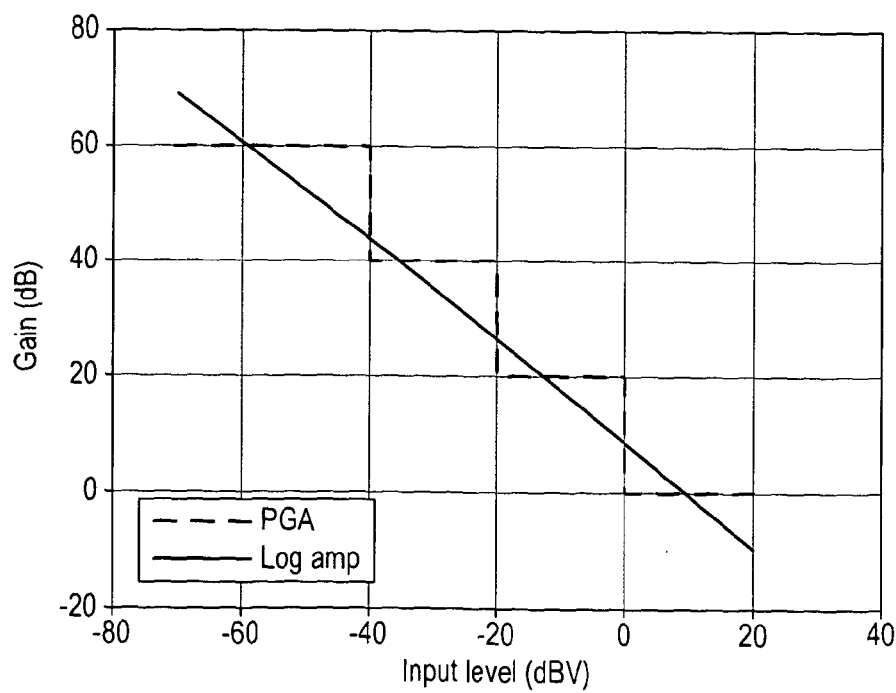

As shown in FIG. 19, the incremental gain of Log Amp (solid line) is inversely proportional to the instantaneous value of the input level, which means the signals dropped in the lower part of the dynamic range will get a larger gain automatically; the signals at the higher part of the dynamic range will get a smaller gain or even an attenuation when the input is more than 2.934V. The incremental gain of PGA is also given in FIG. 19 (the dotted line), which is inversely proportional to the input level totally but in a discrete way.

Figure 20:
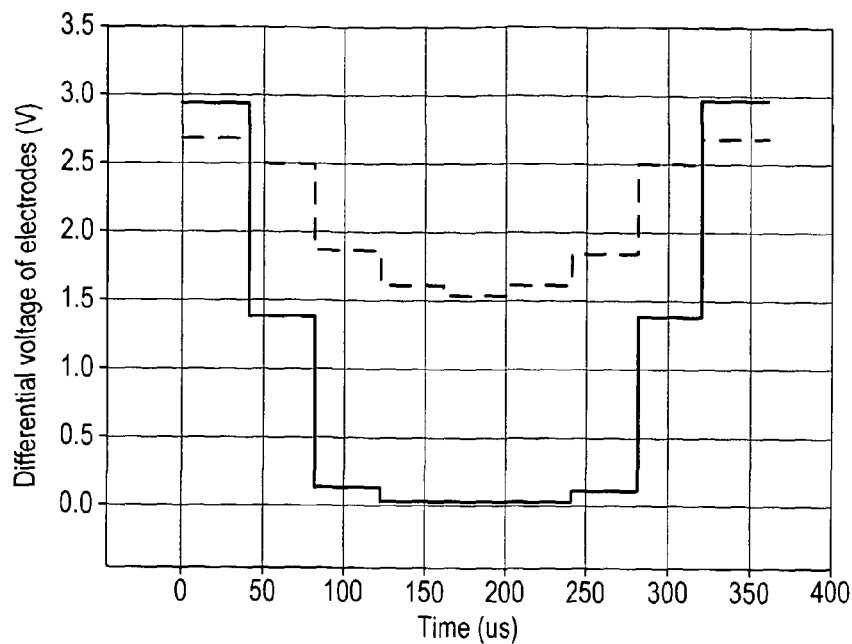

The voltage profile obtained from an ERT measurement after the process of Log Amp is shown in FIG. 20 (the dotted curve). The resultant Log differential voltages have values from 2.6933V to 1.5420V and hence, the dynamic range is compressed dramatically from 38.2 dB to 4.8 dB, which would be very helpful to the improvement of the signal conditioner accuracy.

Figure 21:
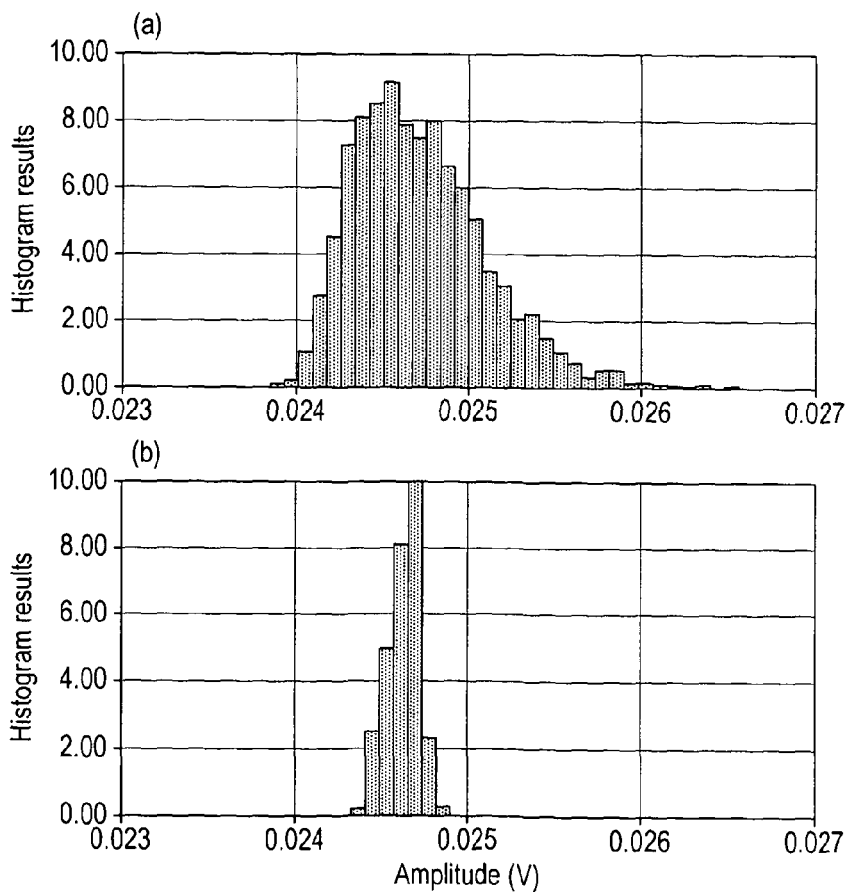

A test was conducted to compare the measurement accuracy without and with a Log Amp. The measurements were obtained from a signal source with fixed amplitude of 25 mV. The histograms graphically summarize the signal amplitude distributions after a large number of repeated measurements. More constricted the distribution is, more accurate the measurement is. The histogram after the Log Amp (FIG. 21 (b)) is better than that of without Log Amp (FIG. 21 (a)).

The low signal-to-noise ratio, high common mode voltage and large dynamic range in the response voltages are three major unfavorable defects to the accurate measurement with an electrical resistance tomography system. The measurement from high conductivity multiphase flows will have more difficulties to a conventional ERT system. Applying the voltage source/current sensing technique to ERT can produce a larger current excitation than the conventional current source. Consequently, larger response voltages appearing on the electrodes are beneficial to enhance the signal-to-noise ratio. The use of the transformer coupling can contribute a higher common mode voltage reject ratio. Finally, the scheme of using logarithmic amplifier in the signal conditioner of ERT system has significant advantages for the process of signal with a wide dynamic range and for the reduction of gain error, as well as the signal settle time than the conventional programmable gain amplifier.

Certain embodiments utilise a method of $k^{th}$ harmonic demodulation for logarithmically processed sinusoidal signal, as follows.

Digital phase sensitive demodulation (PSD) is a classical method to demodulate the sinusoidal response voltages in electrical impedance tomography. However, due to the usage of logarithmic amplifiers in a recently developed compact system embodying the invention, the waveform of logarithmically processed sinusoidal signals is no longer in a form of sine wave. Therefore, the conventional PSD cannot be directly applied. In this description, a method based on $k^{th}$ harmonic demodulation is reported, which has been used to demodulate the logarithmically process sinusoidal signals in an electrical impedance tomography system without the use of inverse process.

Phase Sensitive Demodulation (PSD) is a common method to extract the amplitude and phase information of sinusoidal signal in Electrical Impedance Tomography (EIT). Comparing the analogue PSD, the digital PSD is more straightforward and less sensitive to noise, DC offset and ambient temperature. Particularly, Smith addressed the digital PSD technique based on a digital matched filter technique and demonstrated its maximised signal-to-noise ratio in the presence of Gaussian wideband noise. In order to deal with the voltage profile with the wide dynamic range, the method of logarithmic amplification was used. Since the logarithmically processed sinusoidal signal is non-sinusoidal, the conventional PSD cannot be directly applied. This description briefly reviews PSD and describes a new method based on the $k^{th}$ harmonics demodulation and the Fourier series' coefficients estimation.

Figure 22:
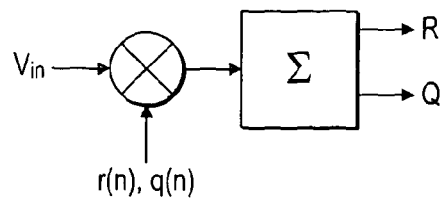

The operation flowchart of digital phase sensitive demodulation is described in FIG. 22.

An analogue sinusoidal signal $V_{in}(t)$ can be expressed in Eq. (1) with an amplitude $V_m$, frequency f and phase $\phi$ $$V_{in}(t) = V_m \sin(\omega t + \phi) \quad (1)$$

The digitalised sampling signals r(n) and q(n) with N samples per period can be denoted by Eq. (2) and (3), which are digital cosine series and sinusoidal series and can be stored in the instrument memory or generated on real-time.

$$r(n) = \cos\left(\frac{2\pi}{N}n\right) \quad (2)$$

$$q(n) = \sin\left(\frac{2\pi}{N}n\right) \quad (3)$$

Within one period, the analogue signal at the same sampling time can be presented by Eq.4

$$V_{in}(n) = V_m\left(\frac{2\pi}{N}n + \varphi\right) \quad (4)$$

Where $n = 1, 2, \ldots, fNt, \ldots, N$.

The real part R and the imaginary part Q of $V_{in}(n)$ can be demodulated with the known sampling series by the operations of multiplication and summation (Kou and Rong 2007):

$$R = \sum_{n=0}^{N-1} V(n)r(n) = \sum_{n=0}^{N-1} V_m \sin\left(\frac{2\pi}{N}n + \varphi\right)\cos\left(\frac{2\pi}{N}n\right) = \frac{1}{2}NV_m\sin\varphi \quad (5)$$

$$Q = \sum_{n=0}^{N-1} V(n)q(n) = \sum_{n=0}^{N-1} V_m \sin\left(\frac{2\pi}{N}n + \varphi\right)\sin\left(\frac{2\pi}{N}n\right) = \frac{1}{2}NV_m\cos\varphi \quad (6)$$

Since R and Q can be sampled and then summed from measurements (the left part of Eq. (5) & (6), eventually, the unknown amplitude, $V_m$, and phase, $\phi$, of $V_{in}(n)$ are deduced from the right parts of the two equations:

$$V_m = \frac{2}{N}\sqrt{R^2 + Q^2} \quad (7)$$

$$\varphi = \arctan\left(\frac{R}{Q}\right) \quad (8)$$

Demodulation from a Rebuilt Inverse Solution

Figure 23:
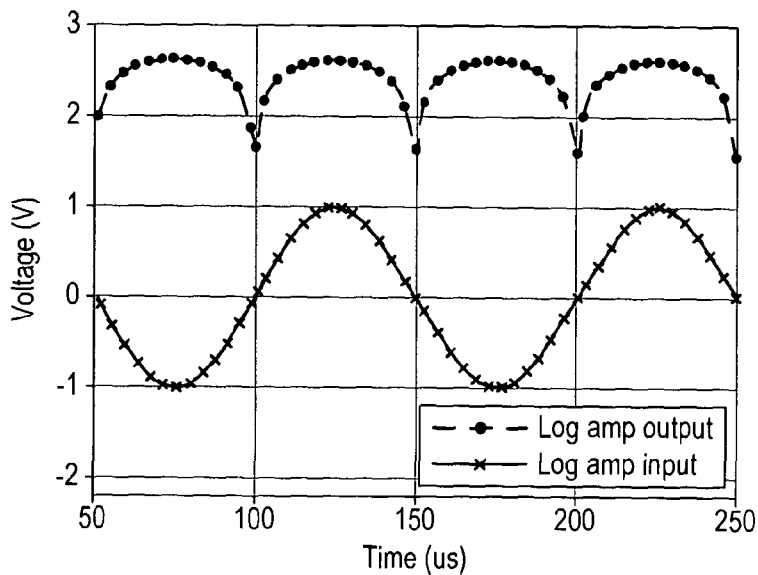

A sinusoidal input of logarithmic amplifier (black solid waveform in FIG. 23 is rectified then transformed into the blue dashed waveform in FIG. 23.

The transformation function of the logarithmic amplifier is described as Eq. (9), in which $V_X$ and $V_Y$ are the adjustable coefficients of logarithmic amplifier. The input of the logarithmic amplifier $V_{in}$ can be computationally rebuilt as Eq. (10) by inversing Eq. (9).

$$V_{out} = V_Y \log\left(\frac{V_{in}}{V_X}\right) \quad (9)$$

$$V_{in} = 10^{\frac{V_{out}}{V_Y} - V_X}{20}} \quad (10)$$

Then the corresponding amplitude and phase information may be extracted from the rebuilt sinusoidal signal with the conventional digital PSD method. However, Eq. (10) is a power function and therefore sensitive to minute variation of coefficients $V_X$ and $V_Y$. Moreover, it is also hard to precisely capture the turning points in order to reverse the interval waveform. Hence, it is not a practicable and preferable method.

Digital Phase Sensitive Demodulation for Logarithmic Output of Sinusoidal Signals Demodulation of $k^{th}$ Harmonic As expressed in Eq. (11), a continuous and periodic waveform can be approximately decomposed into a sum of infinite sinusoidal and cosine waves, namely Fourier series.

$$f(n) = a_0 + \sum_{k=1}^{\infty}\left[a_k\cos\left(k\frac{2\pi}{N}n\right) + b_k\sin\left(k\frac{2\pi}{N}n\right)\right] \quad (11)$$

$$= a_0 + \sum_{k=1}^{\infty} c_k \sin\left(k\frac{2\pi}{N}n + \varphi_k\right)$$

Eq. (11) can be further transformed as the sum of a DC component and the sinusoids with different frequency and phase. The amplitude and phase of $k^{th}$ harmonic is defined as:

$$c_k = \sqrt{a_k^2 + b_k^2} \quad (12)$$

$$\varphi_k = \arctan\left(\frac{a_x}{b_x}\right) \quad (13)$$

In order to obtain the amplitude ($c_k$) and phase ($\phi_k$) of the $k^{th}$ harmonic, the reference signals $r_k(n)$ and $q_k(n)$ with k times fundamental frequency are defined as:

$$r_k(n) = \cos\left(k\frac{2\pi}{N}n\right) \quad (14)$$

$$q_k(n) = \sin\left(k\frac{2\pi}{N}n\right) \quad (15)$$

After the same procedures as that of conventional digital PSD, the real part $R_k$ and imaginary part $Q_k$ of the $k^{th}$ harmonic can be calculated with below equations (Ziemer et al. 1998):

$$R_k = \sum_{n=0}^{N-1} f(n)r_k(n)$$

$$= \sum_{n=0}^{N-1}\left[a_0\cos\left(k\frac{2\pi}{N}n\right) + \sum_{k=1}^{\infty}\left[c_k\sin\left(k\frac{2\pi}{N}n + \varphi_k\right)\right]\cos\left(k\frac{2\pi}{N}n\right)\right]$$

$$= \frac{1}{2}Nc_k\sin\varphi_k \quad (16)$$

$$Q_k = \sum_{n=0}^{N-1} f(n)q_k(n)$$

$$= \sum_{n=0}^{N-1}\left[a_0\sin\left(k\frac{2\pi}{N}n\right) + \sum_{k=1}^{\infty}\left[c_k\sin\left(k\frac{2\pi}{N}n + \varphi_k\right)\right]\sin\left(k\frac{2\pi}{N}n\right)\right]$$

$$= \frac{1}{2}Nc_k\cos\varphi_k \quad (17)$$

The amplitude $c_k$ and phase $\phi_k$ of the $k^{th}$ harmonic can be obtained as below:

$$c_k = \frac{2}{N}\sqrt{R_k^2 + Q_k^2} \quad (18)$$

$$\varphi_k = \arctan\left(\frac{R_k}{Q_k}\right) \quad (19)$$

For instance, an arbitrary discrete function given in Eq. (20) will demonstrate how the above demodulation method extracts the amplitude (¼) and phase ($\pi/6$) of the $2^{nd}$ harmonic component.

$$f(n) = 2 + \frac{1}{2}\cos\left(\frac{2\pi}{N}n + \frac{\pi}{9}\right) + \frac{1}{4}\cos\left(\frac{4\pi}{N}n + \frac{\pi}{6}\right) + \frac{1}{6}\cos\left(\frac{6\pi}{N}n + \frac{\pi}{3}\right) \quad (20)$$

The reference signals having two times fundamental frequency are denoted as:

$$r_2(n) = \cos\left(\frac{4\pi}{N}n\right) \quad (21)$$

$$q_2(n) = \sin\left(\frac{4\pi}{N}n\right) \quad (22)$$

If the number of samples is N=8, after the multiplication and summation (operated as given in Eq. (16) and (17)) are implemented, the real part $R_2$ and imaginary part $Q_2$ of the $2^{nd}$ harmonic are calculated:

$$R_2 = 0.5 \quad (23)$$

$$Q_2 = 0.866 \quad (24)$$

Therefore, the amplitude $c_2$ and phase $\phi_2$ of principal frequency component are detected from Eq. (20).

$$c_2 = \frac{2}{N}\sqrt{R_2^2 + Q_2^2} = \frac{2}{8}\sqrt{0.5^2 + 0.866^2} = \frac{1}{4} \quad (25)$$

$$\varphi_2 = \arctan\left(\frac{R_k}{Q_k}\right) = \frac{\pi}{6} \quad (26)$$

Demodulation of Logarithmically Processed Sinusoidal Signal

Provided that the digitalised sinusoid has amplitude A and phase zero (Eq. (27)), it is rectified within the logarithmic amplifier firstly (Eq. (28)).

$$f(n) = A\sin\left(\frac{2\pi}{N}n\right) \quad (27)$$

$$f_{|sin|}(n) = A\left|\sin\left(\frac{2\pi}{N}n\right)\right| \quad (28)$$

Then, the full-wave rectified sinusoid is transformed to Eq. (29) by the logarithmic amplifier, where $V_Y$ and $V_X$ are the same parameters defined in Eq. (9).

$$f_{log(|sin|)}(n) = V_Y\log\left[\frac{A\left|\sin\left(\frac{2\pi}{N}n\right)\right|}{V_X}\right] \quad (29)$$

Eq. (29) can be expanded in Fourier series as given in Eq. (11) and the coefficients of the series can be calculated with equations given below.

$$a_0 = \frac{1}{T_0}\int_{T_0} V_Y\log\left[\frac{A\left|\sin\left(\frac{2\pi}{N}n\right)\right|}{V_X}\right]dn \quad (30)$$

$$a_k = \frac{2}{T_0}\int_{T_0} V_Y\log\left[\frac{A\left|\sin\left(\frac{2\pi}{N}n\right)\right|}{V_X}\right]\cos\left(k\frac{2\pi}{NT_0}n\right)dn \quad (31)$$

$$b_k = \frac{2}{T_0}\int_{T_0} V_Y\log\left[\frac{A\left|\sin\left(\frac{2\pi}{N}n\right)\right|}{V_X}\right]\sin\left(k\frac{2\pi}{NT_0}n\right)dn \quad (32)$$

After three integrations are computed, the coefficients of Fourier series for function Eq. (29) will be determined. Alternatively, these coefficients can be experimentally obtained using the frequency spectrum analysis method, which decomposes the amplitude and phase of each frequency component with the computational software MATLAB. Whichever is used for the solution, these coefficients will be adopted for all future demodulation as long as the waveform is kept without change.

For instance, the full-wave rectified sinusoid (the blue dashed waveform in FIG. 24) with the amplitude A can be Fourier series expressed by Eq. (33), which indicates the full-wave rectified sinusoid consists of a DC and infinite even order harmonics.

$$f_{|sin|}(n) = \frac{2A}{\pi} + \frac{4A}{\pi} \left[ \frac{\sin\left(\frac{2\pi}{N}n - \frac{\pi}{2}\right)}{1 \cdot 3} + \frac{\sin\left(\frac{4\pi}{N}n - \frac{\pi}{2}\right)}{3 \cdot 5} + \frac{\sin\left(\frac{6\pi}{N}n - \frac{\pi}{2}\right)}{5 \cdot 7} \dots \right]$$

$$= \frac{2A}{\pi} + \frac{4A}{\pi} \sum_{n=1}^{\infty} \frac{1}{4n^2 - 1} \sin\left(\frac{2\pi}{N}n - \frac{\pi}{2}\right)$$

(33)

Figure 25:
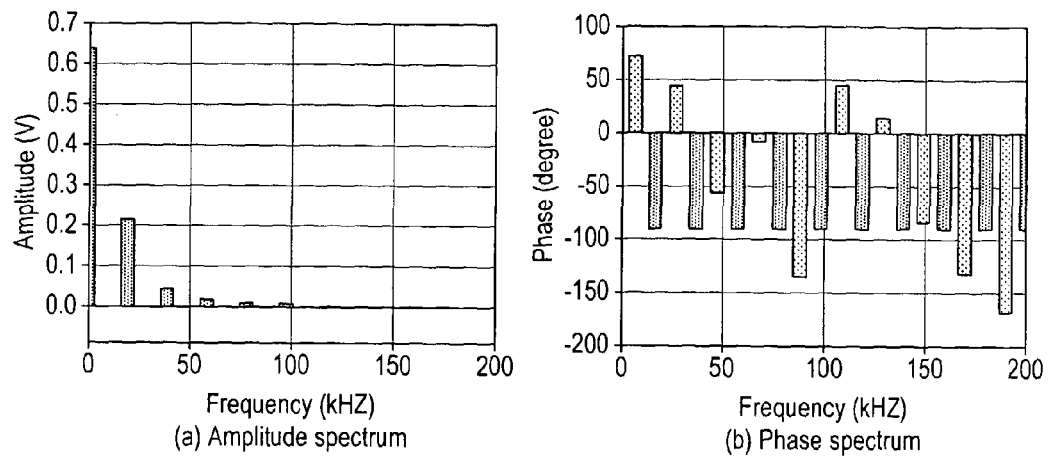

When the frequency and amplitude of an original sinusoidal input signal are 10 kHz and 1V respectively, the amplitude spectrum of its full-wave rectified signal is displayed in FIG. 25(*a*). There are no odd harmonics of 10 kHz and the amplitude of the even harmonics descends which correspond to the Fourier series (Eq. (33)). As highlighted in the phase spectrum (FIG. 25(*b*)), the phase angles of all the even harmonics are −90 degree, in contrast, the phase of odd harmonic varies and it cannot play a practical role because the corresponding amplitude is zero.

Figure 24:
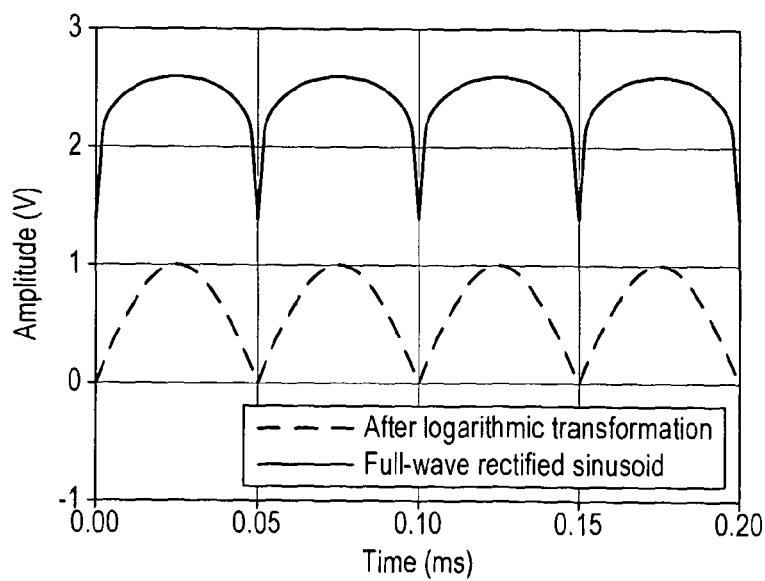
Figure 26:
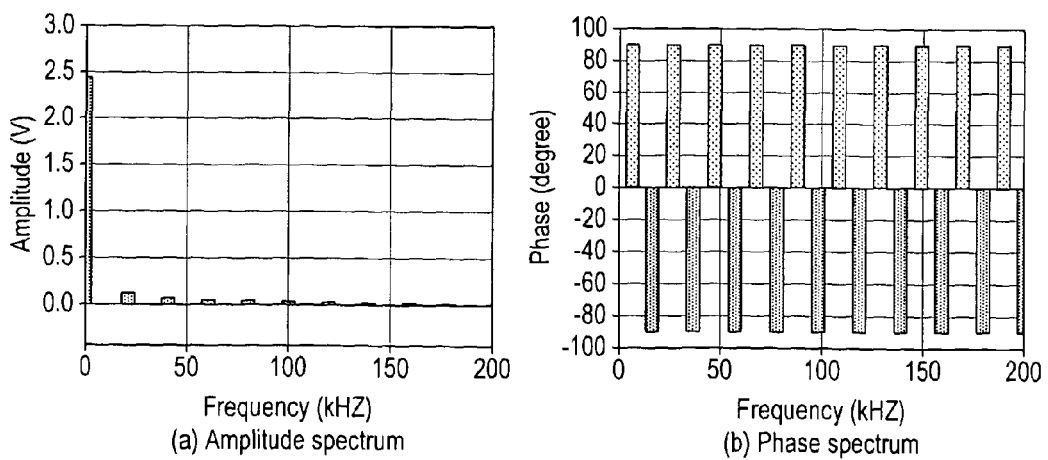

In order to determine the coefficients of the Fourier series, the same frequency spectrum analysis is conducted just once for the output of logarithmic transformation (the black solid waveform in FIG. 24). The amplitude spectrum (FIG. 26(*a*)) demonstrates there are no odd harmonics of 10 kHz either. Compared with the DC component, the amplitude of the even harmonics has small proportions. In the phase spectrum of FIG. 26(*b*), the highlighted phase angles of the even harmonics are −90 degree. The amplitude ratio and phase of the DC and $1^{st}$, $2^{nd}$ and $3^{rd}$ harmonics are tabulated in Table 1.

TABLE 1

Amplitude ratio and phase of main frequency components in logaritmic output

| Frequency component | DC | 1 | 2 | 3 |
|---|---|---|---|---|
| Amplitude ratio | 2.44 | 0.23 | 0.12 | 0.09 |
| Phase angle | 0 | −90 | −90 | −90 |

Based on the results in Table 1, Fourier series of logarithmic output can be constructed as Eq. (34). Comparing the Eq. (33) with Eq. (34), the coefficients in two Fourier series are different but the frequency distribution of harmonics is identical.

$$f_{log(|sin|)}(n) = 2.44 + A\left( \frac{\sin\left(\frac{2\pi n}{N} - \frac{\pi}{2}\right)}{4.39} + \frac{\sin\left(\frac{4\pi n}{N} - \frac{\pi}{2}\right)}{8.09} + \frac{\sin\left(\frac{6\pi n}{N} - \frac{\pi}{2}\right)}{11.25} \dots \right)$$

(34)

The amplitudes and phases of each harmonic have the constant relative relationship with the resultant waveform, no matter how the absolute amplitude and phase of the resultant waveform varies. Therefore, if the amplitude and phase of a certain harmonic is accurately determined, the amplitude and phase of the logarithmic amplifier input could be derived.

Figure 27:
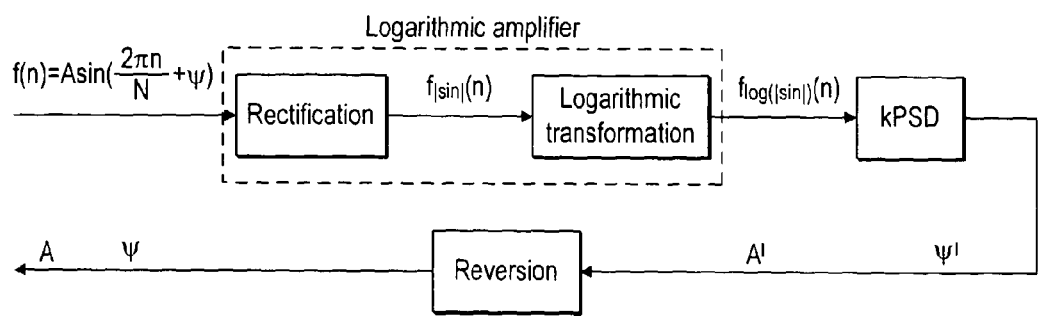

As shown in FIG. 27, if the full-wave rectified sinusoidal input has the amplitude A and phase ψ.

$$f_{|sin|}(n) = A\left|\sin\left(\frac{2\pi n}{N} + \psi\right)\right|$$

(35)

According to Eq. (34), the fundamental frequency component of the logarithmic output has $$\frac{A\sin\left[2\left(\frac{\pi n}{N} + \psi\right) - \frac{\pi}{2}\right]}{4.39} = \frac{A}{4.39}\sin\left[\frac{2\pi n}{N} + \left(2\psi - \frac{\pi}{2}\right)\right]$$

(36)

The amplitude A' and phase ψ' of the fundamental frequency are calculated by the $k^{th}$ harmonic PSD method discussed in section 2.3.

$$A' = \frac{A}{4.39}$$

(37)

$$\psi' = 2\psi - \frac{\pi}{2}$$

(38)

Hence, the amplitude A and phase ψ of the original sinusoid input are derived from Eq. (37) and (38). The logarithmic amplifier input is demodulated.

$$A = 4.39A'$$

(39)

$$\psi = \frac{2\psi' + \pi}{4}$$

(40)

The entire demodulation procedure is illustrated and summarised again in FIG. 27. The sinusoidal input of the logarithmic amplifier has the unknown amplitude A and phase ψ. Due to the logarithmic transformation to the full-wave rectified |f(n)|, the output of the logarithmic amplifier is distorted. The amplitude A' and phase ψ' of $k^{th}$ harmonic are demodulated by applying PSD to the $k^{th}$ harmonic (kPSD). At last, according to the constant amplitude ratio and phase relationship between resultant waveform and harmonic, the amplitude A and phase ψ of initial input f(n) are reversed.

Thus, in certain embodiments a logarithmic amplifier is used for handling the wide dynamic range of response voltage in EIT but it deforms the sinusoid, therefore, the conventional phase sensitive demodulation is not suitable for the use of the logarithmic amplifier. A new method based on $k^{th}$ harmonics demodulation is reported, which has been used to demodulate the logarithmically process sinusoidal signals in an electrical impedance tomography. The Fourier series coefficients of a logarithmic waveform can be determined by either the theoretical computation or the frequency spectrum estimation. The amplitude and phase of the certain order harmonic can be directly demodulated by the kPSD method. Based on the fixed amplitude and phase relationships within harmonics of a certain waveform, the amplitude and phase of the original sinusoidal input signal can demodulated with less sensitive to noise comparing the exponential inverse solution method.

Use of current sensing transformers in certain embodiments is advantageous over using a sense resistor in series with current output, because a sense resistor will introduce an additional common mode voltage and increase the output impedance, therefore, it may generate new error to the measurement.

Certain embodiments provide a voltage source for ERT sensor excitation, which can deliver a large amount of current (350 mA) to high conductive medium.

In certain embodiments the sensor excitation consists of a voltage source, a current sensing circuit and one or more multiplexers to provide current to an ERT sensor (an electrode array). The voltage source is applied to a pair of the electrodes in the ERT sensor by a multiplexer, where the actual current through the ERT sensor is sensed by the current sensing circuit. The differential voltage measurement signals between the electrodes are firstly regulated by the signal conditioning unit to make them suitable for the subsequent circuits. The auxiliary sensors simultaneously sample the temperature and pressure of flow in pipeline for calibration and/or compensation of conductivity measurements. The data acquisition system (DAS) carries out the analogue-to-digital conversion and transmits the data to a PC via a USB 2.0 communication interface. To simplify the system and utilize the advantage of PC technology, most image reconstruction and data analysis will be carried out by a PC.

Known ERT systems adopt current sources to excite the electrodes and then obtain the electrical impedance from voltage measurement. The advantage of the current excitation is the voltage drop on the bulk is despite the presence of electrode-electrolyte impedance if it is assumed that they are in serial connection. However to implement an AC current source with large current and in the high frequency range is difficult. In contrast, embodiments of the invention employ voltage sources to drive currents. When using a voltage source in ERT, it is crucial to measure the consumed current with a high degree of precision in order to obtain absolute bulk resistance measurements. It is also important that the applied voltage remains unchanged over a wide range of load impedances and measurement periods, and therefore the voltage source must have low output impedance. An ideal voltage source with following properties is desirable:

The output impedance is infinitely low as well as to remain constant no matter how the load varies;
The ability to supply current should be as high as possible;
The frequency, amplitude and phase shift of the AC voltage source can be controlled for different demand;
Over-voltage and over-current should be detected swiftly to prevent the system and process from being damaged.

In certain embodiments, AC voltage is coupled to a balanced transformer which operates as a transformation of voltage, and an isolation barrier. Voltage-isolated means that the portion of the measurement channel corresponding to the input signal, multiplexer and output winding of transformer are 'floating', and therefore not referenced or coupled to the measurement instrument ground. The transformer must be capable of transferring the input signal from the input winding to the output winding via electromagnetic coupling with a minimum amount of distortion in amplitude and with immunity to the common mode signal. An important design consideration of the transformer is that the modulated input signal is applied differentially so that the windings have a balanced capacitance, which is important in achieving a high common mode rejection ratio. In addition, isolating a measurement channel requires isolating not only the input signals but also all of the power, clock and control signals provided by the measurement instrument using additional voltage isolation methods.

In certain embodiments, at the time of applying the voltage source, it is necessary to simultaneously measure the applied current and differential voltage from a pair of electrodes to calculate the transimpedance across the whole vessel. The expected features of the current source are the magnitude controllable from 0 mA to 500 mA at the frequency 10 kHz.

There are several methods to measure current. The easiest way is indirect measurement by artificially inserting a resistor in the current path to measure the voltage drop across it, which is proportional to the current through the measured path. Hall effect transducer also can measure current but particularly for large current range, for example 0-10 A or more.

In certain embodiments, a current sensing transformer is used to measure the current value. Current sensing transformer provides non-contact (non-destructive) current measurement. According to the principle of transformer, it has a relationship between the primary and secondary parameters as equation (4.1). The output voltage ($V_{out}$) is an accurate voltage waveform representation of the sensed current ($R_T$) on the primary side (equation (4.2)). Varying the terminating resistance ($R_T$) increases or decreases output voltage/current relationship according to the following equation:

$$N_{sec} = \frac{N_{out}}{N_{in}} = \frac{I_{in}}{I_{out}} = \frac{V_{out}}{V_{in}} \qquad (4.1)$$

$$V_{out} = \frac{R_T \times I_{in}}{N_{sec}} \qquad (4.2)$$

Where $N_{in}$, and $N_{out}$ are the number of turns of the primary coil and secondary coil and $N_{sec}$ is the turn ratio.

In certain embodiments, a logarithmic amplifier rather than the programmable gain amplifier is employed to handle the wide dynamic measurement range. A method based on $K^{th}$ harmonic demodulation is introduced to demodulate the logarithmically processed sinusoidal signals without the use of inverse process. An implementation method to eliminate the transient time of capacitance in the electrode-electrolyte interface is used.

Due to the nature of large dynamic measurement range and complexity of programmable gain amplifier (PGA), a new method of signal conditioning is desirable, and is used in embodiments of the invention. It is known that the logarithmic function is able to greatly compress the input signal range, for example, the graphs with the log scale, rather than uniformly-spaced division, contain much large range. Consequently, a logarithmic amplifier replaces the traditional PGA in certain embodiments to process the voltages measurements before they are converted into digital data by ADC.

The logarithmic amplifier performs a more complex operation than the classical linear amplifier. It converts a signal from one domain of representation to another via a precise non-linear transformation. The essential purpose of the logarithmic amplifier is not only to amplify, but also to compress the wide dynamic range to its decibel equivalent.

There are three major classes of logarithmic amplifiers, DC logarithmic amplifier, true logarithmic amplifier and demodulating logarithmic amplifier.

The first class, the DC Logarithmic amplifier, traditionally operates on slow changing DC signals with bandwidths extending to about 1 MHz. The most popular implementations are to use the logarithmic I-to-V transfer characteristic of the PN junctions of diodes. However, the unipolar input operation narrows its application.

Figure 28:
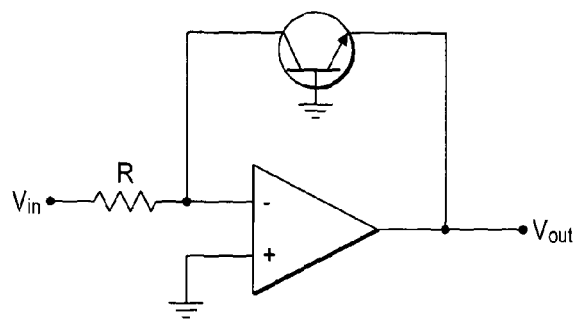

A simple logarithmic amplifier can be made of an operational amplifier and bipolar junction transistor, as shown in FIG. 28.

With the exponential relationship between the collector current and emitter-base voltage, the output ($V_{out}$) and input ($V_{in}$) relation of logarithmic amplifier is stated below [86]:

$$V_{out} = -V_T \ln \frac{V_{in}}{I_{SO}R} \qquad (5.41)$$

where $V_T$ is the thermal voltage of transistor, $I_{SO}$ is its saturation current.

Due to the characteristic of logarithmic function, the input voltage in equation (5.41) has to be positive. It is clear that the value of thermal voltage, $V_T$, depends on temperature, which will affect the consistence of output. These two drawbacks disable the usage of the first type of logarithmic amplifier for this system.

The second class of logarithmic amplifier is known as the baseband logarithmic amplifier. The amplifier provides an output proportional to the logarithm of the instantaneous input signal. A special version of the baseband logarithmic amplifier is the "true logarithmic amplifier", which accepts bipolar inputs and provides a compressed output voltage that preserves the polarity of the input. Finally, the third class of logarithmic amplifier is the demodulating logarithmic amplifier (AD8310), which is utilised in the voltage-applied ERT system to compress AC input signals, yielding the logarithm of the rectified signal's envelope.

Because of the existence of fluid's capacitance and systematic stray capacitance in ERT, the phase delay between excitation and response signals is always introduced The function of signal demodulation is to extract the resistive (in-phase or real) component and the capacitive (quadrature or imaginary) component for reconstruction of relevant impedance component images.

The invention claimed is:

1. Electrical tomography apparatus comprising:
a first electrode;
a second electrode; and
current driving means for driving an electrical current between the first electrode and the second electrode through a medium,
wherein the current driving means comprises:
a first transformer having a first winding and a second winding, the second winding having a first terminal and a second terminal; and
means for generating an alternating current through the first winding so as to generate an alternating voltage between said first terminal and said second terminal,
the apparatus further comprising connecting means arranged to connect the first terminal to the first electrode and the second terminal to the second electrode, whereby generation of the alternating current in the first winding results in generation of an alternating voltage between the first and second electrodes, and current sensing means arranged to provide a current signal indicative of current flowing through said second winding, the current sensing means comprising:
a second transformer having a primary winding and a secondary winding arranged such that an alternating current flowing in the primary winding generates a corresponding alternating voltage across the secondary winding, the primary winding being connected in series with the second winding of the first transformer such that the same current flows through the second and primary windings, and a voltage developed across the secondary winding providing said current signal.

2. Apparatus in accordance with claim 1, wherein the current sensing means further comprises a resistor connected in parallel across the secondary winding.

3. Apparatus in accordance with claim 1, wherein the primary winding comprises N terms and the secondary winding comprises kN terms, where k is at least 100.

4. Apparatus in accordance with claim 1, further comprising first amplification means arranged to generate a first amplified signal from said current signal, the first amplification means comprising a first logarithmic amplifier.

5. Apparatus in accordance with claim 4, wherein the first amplification means comprises a first pre-amplifier arranged to amplify the current signal and provide the amplified current signal as an input signal to the first logarithmic amplifier.

6. Apparatus in accordance with claim 4, wherein said first amplified signal is an output signal of said first logarithmic amplifier.

7. Apparatus in accordance with claim 4, further comprising a third electrode and a fourth electrode and second amplification means arranged to generate a second amplified signal from a voltage signal corresponding to or indicative of a voltage developed between the third and fourth electrodes as a result of said electrical current being driven between the first and second electrodes through said medium.

8. Apparatus in accordance with claim 7, wherein the second amplification means comprises a second logarithmic amplifier.

9. Apparatus in accordance with claim 8, wherein the second amplification means comprises a second pre-amplifier arranged to amplify said voltage signal and provide the amplified voltage signal as an input signal to the second logarithmic amplifier.

10. Apparatus in accordance with claim 8, wherein said second amplified signal is an output signal of the second logarithmic amplifier.

11. Apparatus in accordance with claim 8, further comprising means for generating a difference signal indicative of a difference between the first amplified signal and the second amplified signal.

12. Apparatus in accordance with claim 11, wherein the means for generating a difference signal comprises a differential amplifier arranged to receive the first amplified signal as a first input signal and the second amplified signal as a second input signal.

13. Apparatus in accordance with claim 11, further comprising converting means for converting said difference signal to a digital difference signal, and processing means arranged to process said digital difference signal.

14. Apparatus in accordance with claim 1, wherein said connecting means comprises a multiplexer controllable to selectively connect the first and second terminals to a pair of electrodes selected from a plurality of electrodes including the first and second electrodes.

15. Apparatus in accordance with claim 1, further comprising a controller for adjusting a phase of the alternating current generated in said first winding.

16. Apparatus in accordance with claim 15, wherein said controller is arranged to adjust said phase of the alternating current according to a phase of said difference signal.

17. Apparatus in accordance with claim 16, wherein said controller is configured to determine said phase of the difference signal.

18. Apparatus in accordance with claim 1, further comprising containment means for containing a fluidic medium to be evaluated, and wherein the first and second electrodes are attached to the containment means so as to be in contact with a fluidic medium contained in the containment means.

19. An electrical tomography method for evaluating a medium, the method comprising:
   driving an electrical current through the medium and detecting a resultant electrical voltage,
   characterised in that said driving comprises generating an alternating voltage between a pair of current-driving electrodes by generating an alternating current in a first winding of a first transformer to generate an alternating voltage across terminals of a second winding of the transformer, and connecting said terminals to said pair of electrodes, the method further comprising sensing the current driven through the medium using a second transformer having a primary winding, arranged in series with the second winding of the first transformer, and a secondary winding arranged such that a voltage generated across the secondary winding provides a current signal indicative of the current drive through the medium.

20. A method in accordance with claim 19, further comprising:
   using first amplification means to generate a first amplified signal indicative of a logarithm of the electrical current driven through the medium;
   using second amplification means to generate a second amplified signal indicative of a logarithm of the resultant electrical voltage; and
   generating a difference signal indicative of a difference between the first amplified signal and the second amplified signal.

21. A method in accordance with claim 20, further comprising:
   determining a phase of said difference signal; and
   adjusting a phase of the alternating current in the first winding according to the phase of the difference signal.

22. Apparatus for driving electrical current between a pair of electrodes via a medium, the apparatus comprising:
   a first transformer having a first winding and a second winding;
   means for generating an alternating current through the first winding so as to generate an alternating voltage across the second winding; and
   current sensing means comprising a second transformer having a primary winding, connected in series with the second winding of the first transformer, and a secondary winding arranged such that a voltage developed across the secondary winding is indicative of current flow in the second and primary windings.

23. Apparatus in accordance with claim 22, further comprising a logarithmic amplifier arranged to amplify the voltage developed across the secondary winding.

24. Electrical tomography apparatus comprising apparatus in accordance with claim 22 and connecting means arranged to connect a pair of electrodes to the second and primary windings.

25. Electrical test apparatus for evaluating at least one electrical property of a medium, the test apparatus comprising:
   apparatus in accordance with claim 22 arranged to drive an electrical current between first and second electrodes through the medium and to sense the current driven through the medium; and
   voltage sensing means arranged to sense a voltage developed across the medium as a result of the current driven through the medium.

26. Electrical test apparatus in accordance with claim 25, further comprising:
   first amplification means arranged to generate a first amplified signal indicative of a logarithm of the electrical current driven through the medium;
   second amplification means arranged to generate a second amplified signal indicative of a logarithm of the voltage developed across the medium; and
   means for generating a difference signal indicative of a difference between the first amplified signal and the second amplified signal,
   whereby the difference signal is indicative of an impedance.

* * * * *